(12) United States Patent
Smith et al.

(10) Patent No.: US 11,510,808 B2
(45) Date of Patent: Nov. 29, 2022

(54) SYSTEMS, DEVICES AND METHODS FOR CALORIC VESTIBULAR STIMULATION HAVING AN IMPEDANCE MONITOR AND/OR TEMPERATURE SENSOR

(71) Applicant: Scion NeuroStim, Inc., Durham, NC (US)

(72) Inventors: Lanty L. Smith, Raleigh, NC (US);
Leseo L. Rogers, Raleigh, NC (US);
Robert D. Black, Chapel Hill, NC (US)

(73) Assignee: Scion NeuroStim, Inc., Durham, NC (US)

( * ) Notice: Subject to any disclaimer, the term of this patent is extended or adjusted under 35 U.S.C. 154(b) by 229 days.

(21) Appl. No.: 16/883,007

(22) Filed: May 26, 2020

(65) Prior Publication Data
US 2021/0137730 A1 May 13, 2021

Related U.S. Application Data

(63) Continuation of application No. 15/467,596, filed on Mar. 23, 2017, now Pat. No. 10,660,792, which is a continuation of application No. 13/525,817, filed on Jun. 18, 2012, now Pat. No. 9,655,772, which is a continuation-in-part of application No.
(Continued)

(51) Int. Cl.
*A61F 7/12* (2006.01)
*A61N 2/00* (2006.01)
*A61F 7/00* (2006.01)
*A61N 1/36* (2006.01)
(Continued)

(52) U.S. Cl.
CPC ............... *A61F 7/12* (2013.01); *A61F 7/007* (2013.01); *A61N 2/002* (2013.01); *A61N 2/006* (2013.01); *A61B 2018/00875* (2013.01); *A61F 2007/0005* (2013.01); *A61F 2007/0075* (2013.01); *A61F 2007/0093* (2013.01);
(Continued)

(58) Field of Classification Search
CPC ... A61B 2018/00875; A61F 2007/0005; A61F 2007/0075; A61F 2007/0093; A61F 2007/0095; A61F 2007/0096; A61F 2007/0296; A61F 7/007; A61F 7/12; A61N 1/36036; A61N 2/002; A61N 2/006
See application file for complete search history.

(56) References Cited

U.S. PATENT DOCUMENTS

| | | | |
|---|---|---|---|
| 2007/0123795 A1* | 5/2007 | Kopke | A61B 5/291 600/559 |
| 2010/0198282 A1* | 8/2010 | Rogers | A61F 7/007 607/3 |

* cited by examiner

*Primary Examiner* — Ankit D Tejani
(74) *Attorney, Agent, or Firm* — Myers Bigel, P.A.

(57) ABSTRACT

An in-ear stimulation device for administering caloric stimulation to the ear canal of a subject includes (a) first and second earpieces configured to be insertable into the ear canals of the subject; (b) at least first and second thermoelectric devices thermally coupled to respective ones of the first and second earpieces; (c) a first heat sink thermally coupled to the first thermoelectric device opposite the first earpiece and a second heat sink thermally coupled to the second thermoelectric device opposite the second earpiece; and (d) a controller comprising a waveform generator in communication with the first and second thermoelectric devices, the waveform generator configured to generate a first control signal to control a first caloric output to the first thermoelectric device and a second control signal to control a second caloric output to the second caloric device.

1 Claim, 19 Drawing Sheets

Related U.S. Application Data

PCT/US2011/065396, filed on Dec. 16, 2011, which is a continuation-in-part of application No. 12/970,312, filed on Dec. 16, 2010, now Pat. No. 8,460,356, and a continuation-in-part of application No. PCT/US2010/060771, filed on Dec. 16, 2010, and a continuation-in-part of application No. 12/970,347, filed on Dec. 16, 2010, now Pat. No. 8,603,152, and a continuation-in-part of application No. PCT/US2010/060764, filed on Dec. 16, 2010.

(60) Provisional application No. 61/498,911, filed on Jun. 20, 2011, provisional application No. 61/498,943, filed on Jun. 20, 2011, provisional application No. 61/498,131, filed on Jun. 17, 2011, provisional application No. 61/498,096, filed on Jun. 17, 2011, provisional application No. 61/498,080, filed on Jun. 17, 2011, provisional application No. 61/497,761, filed on Jun. 16, 2011, provisional application No. 61/434,474, filed on Dec. 17, 2010, provisional application No. 61/424,132, filed on Dec. 17, 2010, provisional application No. 61/242,326, filed on Sep. 14, 2009.

(51) Int. Cl.
*A61B 18/00* (2006.01)
*A61F 7/02* (2006.01)

(52) U.S. Cl.
CPC ............... *A61F 2007/0095* (2013.01); *A61F 2007/0096* (2013.01); *A61F 2007/0296* (2013.01); *A61N 1/36036* (2017.08)

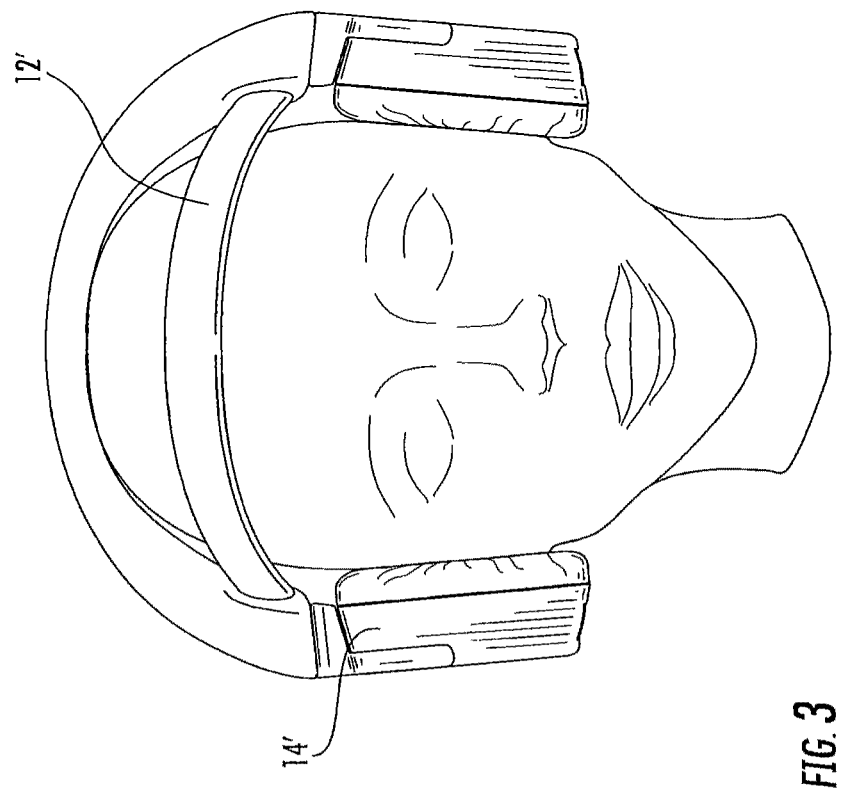
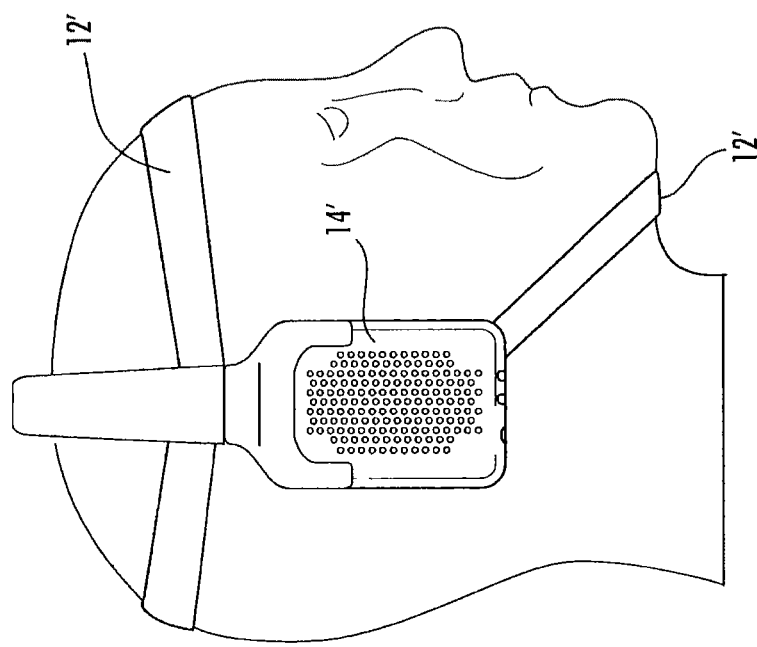
FIG. 3

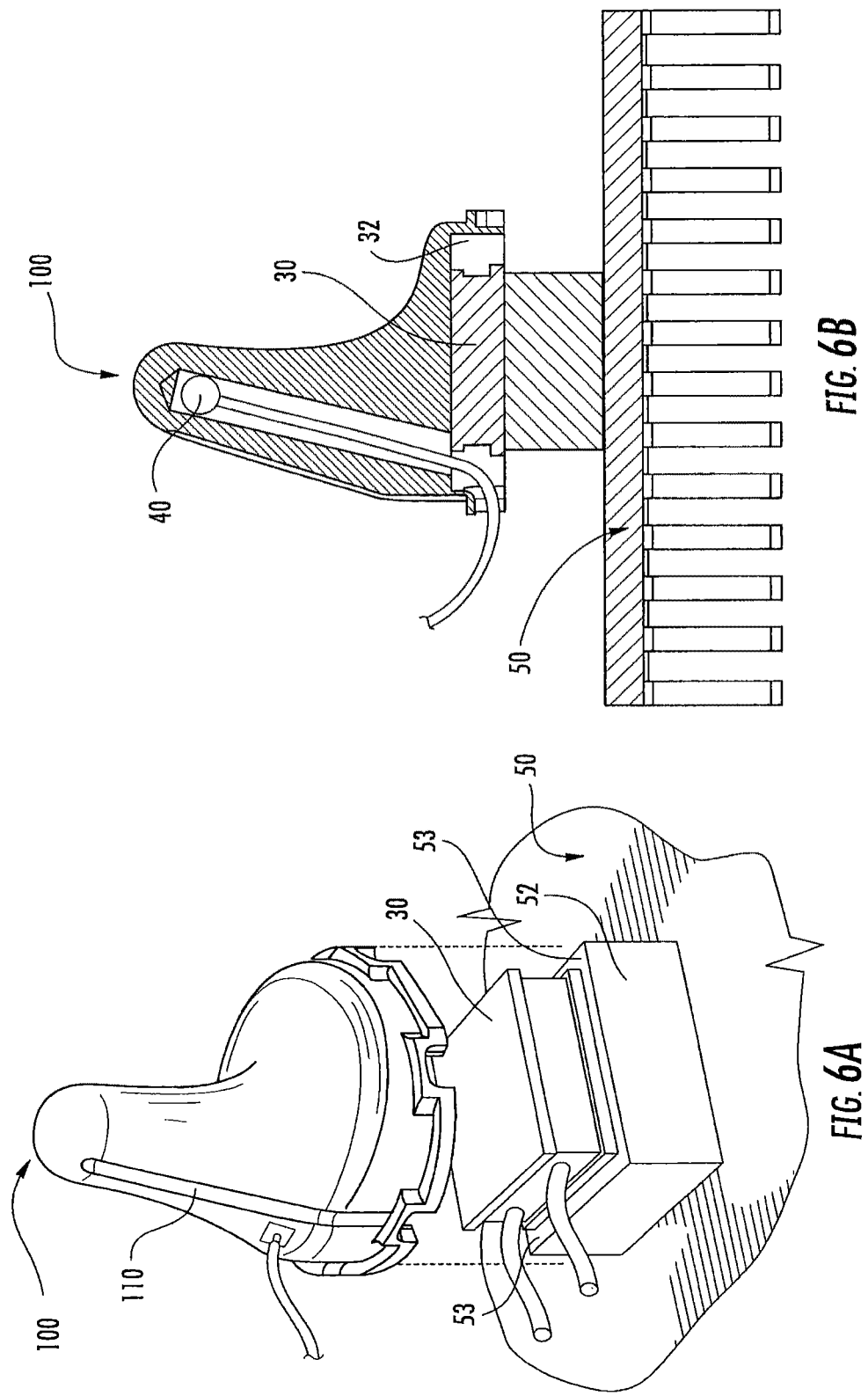

SYSTEMS, DEVICES AND METHODS FOR CALORIC VESTIBULAR STIMULATION HAVING AN IMPEDANCE MONITOR AND/OR TEMPERATURE SENSOR

RELATED APPLICATIONS

This application is a continuation of U.S. patent application Ser. No. 15/467,596 filed Mar. 23, 2017 which is a continuation of U.S. patent application Ser. No. 13/525,817 filed on Jun. 18, 2012 which is a continuation in part of PCT/US2011/065396, filed on Dec. 16, 2011, which application claims priority to United States Provisional Patent Application Nos. 61/424,474, filed Dec. 17, 2010; 61/498,131, filed Jun. 17, 2011; 61/497,761, filed Jun. 16, 2011; 61/424,132, filed Dec. 17, 2010; 61/498,096, filed Jun. 17, 2011; 61/424,326, filed Dec. 17, 2010; 61/498,080, filed Jun. 17, 2011; 61/498,911, filed Jun. 20, 2011 and 61/498,943, filed Jun. 20, 2011; and is a continuation in part of U.S. patent application Ser. No. 12/970,312, filed Dec. 16, 2010 and Ser. No. 12/970,347, filed Dec. 16, 2010 and PCT Application Nos. PCT/US2010/060764, filed Dec. 16, 2010, PCT/US2010/060771, filed Dec. 16, 2010, the disclosure of each of which is incorporated herein by reference in its entirety. This application is related to application Ser. No. 13/525,765, filed Jun. 18, 2012

FIELD OF THE INVENTION

The present invention relates to caloric vestibular stimulation, and in particular, to bilateral caloric vestibular stimulation.

BACKGROUND

Caloric vestibular stimulation ("CVS") has long been known as a diagnostic procedure for testing the function of the vestibular system. In the traditional hospital setting, water caloric tests are used to assess levels of consciousness during acute or chronic brain injury. The brain injury may be due to head trauma or a central nervous system event such as a stroke. Other brain injuries occur in the presence of metabolic abnormalities (e.g., kidney disease, diabetes), seizures, or toxic levels of controlled substances or alcohol.

U.S. Patent Publication No. 2003/0195588 to Fischell et al. discusses a stimulator in an ear canal that is adapted to provide magnetic, electrical, audible, tactile or caloric stimulation. Fischell proposes a ring-shaped caloric transducer strip on an ear canal sensor/stimulator system that may result in relatively slow thermal changes of the ear canal.

Accordingly, apparatuses and associated methods useful for delivering stimulation to the nervous system and/or the vestibular system of an individual that may be capable of relatively fast temperature changes are potentially beneficial to take full advantage of physiological responses that are useful in diagnosing and/or treating a variety of medical conditions.

SUMMARY OF EMBODIMENTS OF THE INVENTION

In some embodiments, an in-ear stimulation device for administering caloric stimulation to the ear canal of a subject includes (a) first and second earpieces configured to be insertable into the ear canals of the subject; (b) at least first and second thermoelectric devices thermally coupled to respective ones of the first and second earpieces; (c) a first heat sink thermally coupled to the first thermoelectric device opposite the first earpiece and a second heat sink thermally coupled to the second thermoelectric device opposite the second earpiece; (d) an electrical connection that electrically connects the first and second earpieces, and (e) a controller comprising an impedance monitor configured to measure an impedance value between the first and second earpieces and to determine whether the first and second earpieces are inserted into the ear canals of the subject responsive to the impedance value.

In some embodiments, the impedance value comprises resistive and capacitive components.

In some embodiments, the impedance monitor is configured to correlate the impedance value with a thermal impedance and/or thermal conductance of an interface between the first and second earpieces and the ear canal of the subject.

In some embodiments, the electrical connection comprises a metal wire that electrically connects the first and second earpieces.

In some embodiments, the controller further comprises a waveform generator in communication with the first and second thermoelectric device. The waveform generator is configured to generate a first control signal to control a first caloric output to the first thermoelectric device and a second control signal to control a second caloric output to the second thermoelectric device. The controller may include a memory configured to store waveform data and/or impedance values, and a patient module that is configured to determine whether a subject has complied with a treatment plan based on whether the stored impedance values are consistent with the first and second earpieces being correctly positioned during administration of the treatment.

In some embodiments, the impedance module is configured to deliver an electrical current via the electrical connector to one of the first and second earpieces. The impedance module may be configured to detect whether the first and second earpieces and the subject form a closed circuit or an open circuit, and a closed circuit indicates a higher degree of thermal contact between the first and second earpieces than an open circuit. The impedance module may be configured to determine if a degree of thermal contact between the earpieces and the subject is sufficient by determining whether the impedance value is within a predefined range. The impedance module may be configured to provide feedback to the waveform module such that the waveform module increases or decreases an amplitude of the first and second waveform control signals in response to a degree of thermal contact determined by the impedance module based on the impedance value of the electrical connector.

In some embodiments, an in-ear stimulation device for administering caloric stimulation to the ear canal of a subject includes (a) at least one earpiece configured to be insertable into the ear canal of the subject; (b) at least one thermoelectric devices thermally coupled to the at least one earpiece; (c) a first heat sink thermally coupled to the at least one thermoelectric device opposite the at least one earpiece earpiece; (d) a temperature sensor thermally coupled to the at least one earpiece, and (e) a controller comprising a temperature monitor configured to measure a temperature value of the at least one earpiece and to determine whether the at least one earpiece is inserted into the ear canal of the subject responsive to the temperature value.

In some embodiments, the controller further includes a waveform generator in communication with the at least one thermoelectric device, the waveform generator configured to generate a control signal to control a caloric output to the at least one thermoelectric device.

In some embodiments, the temperature monitor is configured to determine that the at least one earpiece is inserted into the ear canal of the subject when a temperature value increases prior to delivery of a control signal by the waveform generator, and the temperature monitor is configured to determine that the at least one earpiece is not inserted into the ear canal of the subject when a temperature value does not increase prior to delivery of a control signal by the waveform generator.

In some embodiments, the temperature monitor is configured to determine that the at least one earpiece is inserted into the ear canal of the subject when a number of cycles during a delivery of a control signal by the waveform generator is less than a number of cycles during delivery of the control signal when the earpiece is not inserted into the ear.

In some embodiments, the temperature monitor is configured to compare the control signal from the waveform generator with the temperature output and to determine a degree of thermal contact between the earpiece and the ear canal based on a lag time between a temperature driven by the control signal and the temperature output. A longer delay between a temperature driven by the control signal and the temperature output may indicate an increased thermal contact compared to a shorter delay between the control signal and the temperature output.

In some embodiments, an in-ear stimulation method for administering caloric stimulation to the ear canal of a subject includes positioning at least a portion of an in-ear stimulation device in the ear canals of the subject. The in-ear stimulation device includes (a) first and second earpieces configured to be insertable into the ear canals of the subject; (b) at least first and second thermoelectric devices thermally coupled to respective ones of the first and second earpieces; (c) a first heat sink thermally coupled to the first thermoelectric device opposite the first earpiece and a second heat sink thermally coupled to the second thermoelectric device opposite the second earpiece; and (d) an electrical connection that electrically connects the first and second earpieces. An impedance monitor measures an impedance value between the first and second earpieces. Whether the first and second earpieces are inserted into the ear canals of the subject is determined responsive to the impedance value.

In some embodiments, the impedance value includes resistive and capacitive components. In some embodiments, the impedance value is correlated with a thermal impedance and/or thermal conductance of an interface between the first and second earpieces and the ear canal of the subject.

In some embodiments, the electrical connection comprises a metal wire that electrically connects the first and second earpieces.

In some embodiments, a waveform generator generates a first control signal to control a first caloric output to the first thermoelectric device and a second control signal to control a second caloric output to the second thermoelectric device. In some embodiments, waveform data and/or impedance values are stored, and whether a subject has complied with a treatment plan is determined based on whether the stored impedance values are consistent with the first and second earpieces being correctly positioned during administration of the treatment.

In some embodiments, an electrical current is delivered via the electrical connector to one of the first and second earpieces. Whether the first and second earpieces and the subject form a closed circuit or an open circuit may be determined, and a closed circuit indicates a higher degree of thermal contact between the first and second earpieces than an open circuit. Whether a degree of thermal contact between the earpieces and the subject is sufficient may be determined based on whether the impedance value is within a predefined range.

In some embodiments, feedback is provided to the waveform module such that the waveform module increases or decreases an amplitude of the first and second waveform control signals in response to a degree of thermal contact determined by the impedance module based on the impedance value of the electrical connector.

In some embodiments, an in-ear stimulation method for administering caloric stimulation to the ear canal of a subject includes positioning at least a portion of an in-ear stimulation device in the ear canals of the subject. The in-ear stimulation device includes (a) at least one earpiece configured to be insertable into the ear canal of the subject; (b) at least one thermoelectric devices thermally coupled to the at least one earpiece; (c) a first heat sink thermally coupled to the at least one thermoelectric device opposite the at least one earpiece earpiece; and (d) a temperature sensor thermally coupled to the at least one earpiece. A temperature value of the at least one earpiece may be measured. Whether the at least one earpiece is inserted into the ear canal of the subject may be determined responsive to the temperature value.

In some embodiments, the method includes generating a control signal with a waveform generator to control a caloric output to the at least one thermoelectric device.

In some embodiments, the method includes determining that the at least one earpiece is inserted into the ear canal of the subject when a temperature value increases prior to delivery of a control signal by the waveform generator, and determining that the at least one earpiece is not inserted into the ear canal of the subject when a temperature value does not increase prior to delivery of a control signal by the waveform generator.

In some embodiments, the method includes determining that the at least one earpiece is inserted into the ear canal of the subject when a number of cycles during a delivery of a control signal by the waveform generator is less than a number of cycles during delivery of the control signal when the earpiece is not inserted into the ear.

In some embodiments, the method includes comparing the control signal from the waveform generator with the temperature output and to determine a degree of thermal contact between the earpiece and the ear canal based on a lag time between a temperature driven by the control signal and the temperature output.

In some embodiments, a longer delay between a temperature driven by the control signal and the temperature output indicates increased thermal contact compared to a shorter delay between the control signal and the temperature output.

BRIEF DESCRIPTION OF THE DRAWINGS

The accompanying drawings, which are incorporated in and constitute a part of the specification, illustrate embodiments of the invention and, together with the description, serve to explain principles of the invention.

FIG. 3 is a front and side view of a bilateral caloric vestibular stimulation device according to some embodiments of the present invention;

FIG. 6A is an exploded perspective view of an earpiece and heat sink according to some embodiments of the present invention;

FIG. 6B is a side view of an earpiece and heat sink according to some embodiments of the present invention;

DETAILED DESCRIPTION OF EMBODIMENTS OF THE INVENTION

Figure 1:
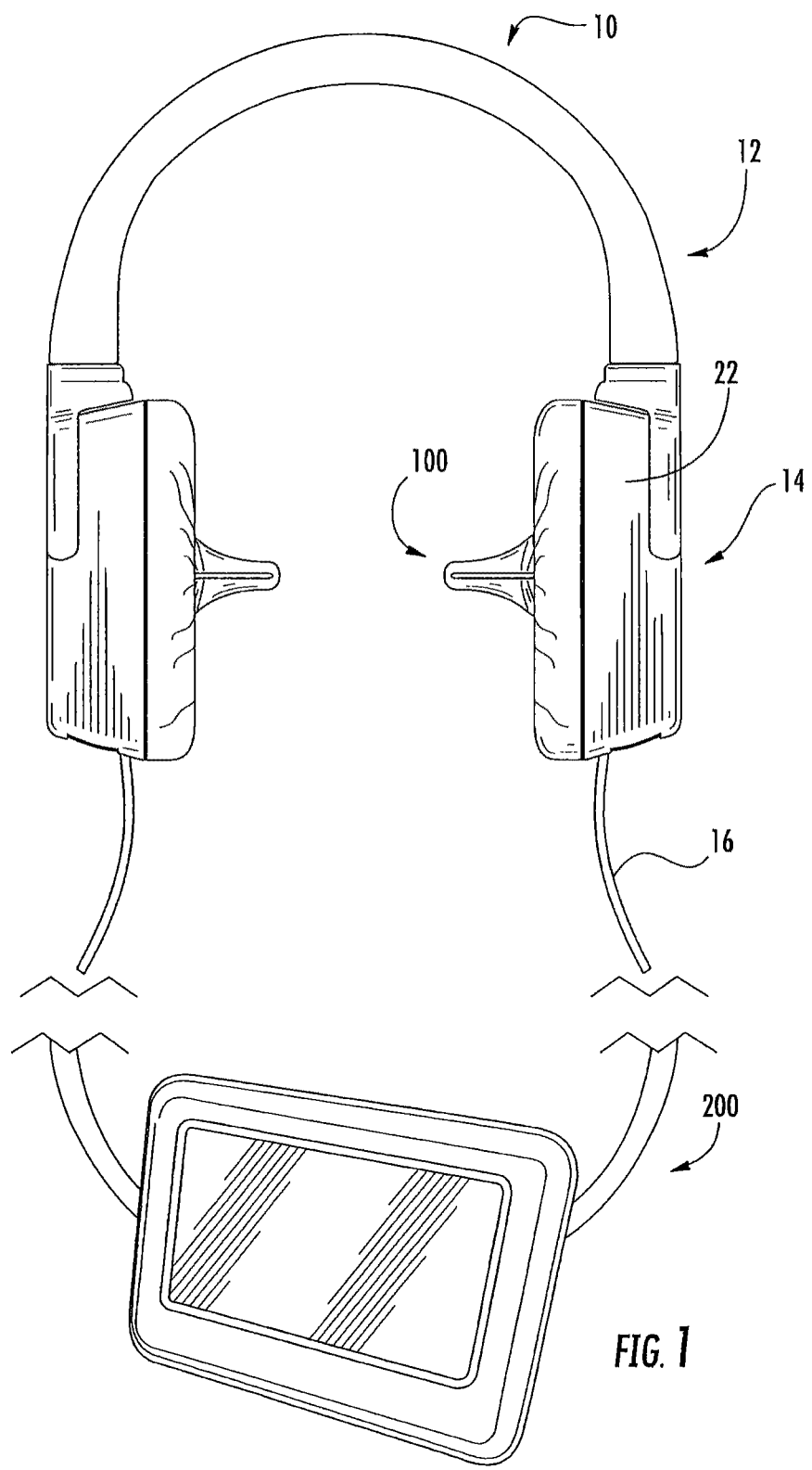
FIG. 1 is a side view of a bilateral caloric vestibular stimulation device and controller according to some embodiments of the present invention.

The present invention now will be described hereinafter with reference to the accompanying drawings and examples, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity.

Definitions

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of "over" and "under." The device may be otherwise oriented (rotated 90 degrees or at other orientations) and the spatially relative descriptors used herein interpreted accordingly. Similarly, the terms "upwardly," "downwardly," "vertical," "horizontal" and the like are used herein for the purpose of explanation only unless specifically indicated otherwise.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present invention. The sequence of operations (or steps) is not limited to the order presented in the claims or figures unless specifically indicated otherwise.

The present invention is described below with reference to block diagrams and/or flowchart illustrations of methods, apparatus (systems) and/or computer program products according to embodiments of the invention. It is understood that each block of the block diagrams and/or flowchart illustrations, and combinations of blocks in the block diagrams and/or flowchart illustrations, can be implemented by computer program instructions. These computer program instructions may be provided to a processor of a general purpose computer, special purpose computer, and/or other programmable data processing apparatus to produce a machine, such that the instructions, which execute via the processor of the computer and/or other programmable data processing apparatus, create means for implementing the functions/acts specified in the block diagrams and/or flowchart block or blocks.

These computer program instructions may also be stored in a computer-readable memory that can direct a computer or other programmable data processing apparatus to function in a particular manner, such that the instructions stored in the computer-readable memory produce an article of manufacture including instructions which implement the function/act specified in the block diagrams and/or flowchart block or blocks.

The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions/acts specified in the block diagrams and/or flowchart block or blocks.

Accordingly, the present invention may be embodied in hardware and/or in software (including firmware, resident software, micro-code, etc.). Furthermore, embodiments of the present invention may take the form of a computer program product on a computer-usable or computer-readable non-transient storage medium having computer-usable or computer-readable program code embodied in the medium for use by or in connection with an instruction execution system.

The computer-usable or computer-readable medium may be, for example but not limited to, an electronic, optical, electromagnetic, infrared, or semiconductor system, apparatus, or device. More specific examples (a non-exhaustive list) of the computer-readable medium would include the following: an electrical connection having one or more wires, a portable computer diskette, a random access memory (RAM), a read-only memory (ROM), an erasable programmable read-only memory (EPROM or Flash memory such as an SD card), an optical fiber, and a portable compact disc read-only memory (CD-ROM).

As used herein, the term "vestibular system" has the meaning ascribed to it in the medical arts and includes but is not limited to those portions of the inner ear known as the vestibular apparatus and the vestibulocochlear nerve. The vestibular system, therefore, further includes, but is not limited to, those parts of the brain that process signals from the vestibulocochlear nerve.

"Treatment," "treat," and "treating" refer to reversing, alleviating, reducing the severity of, delaying the onset of, inhibiting the progress of, or preventing a disease or disorder as described herein, or at least one symptom of a disease or disorder as described herein (e.g., treating one or more of tremors, bradykinesia, rigidity or postural instability associated with Parkinson's disease; treating one or more of intrusive symptoms (e.g., dissociative states, flashbacks, intrusive emotions, intrusive memories, nightmares, and night terrors), avoidant symptoms (e.g., avoiding emotions, avoiding relationships, avoiding responsibility for others, avoiding situations reminiscent of the traumatic event), hyperarousal symptoms (e.g., exaggerated startle reaction, explosive outbursts, extreme vigilance, irritability, panic symptoms, sleep disturbance) associated with post-traumatic stress disorder). In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved—for example, to prevent or delay their recurrence. Treatment may comprise providing neuroprotection, enhancing cognition and/or increasing cognitive reserve. Treatment may be as an adjuvant treatment as further described herein.

"Adjuvant treatment" as described herein refers to a treatment session in which the delivery of one or more thermal waveforms to the vestibular system and/or the nervous system of a patient modifies the effect(s) of one or more active agents and/or therapies. For example, the delivery of one or more thermal waveforms to the vestibular system and/or the nervous system of a patient may enhance the effectiveness of a pharmaceutical agent (by restoring the therapeutic efficacy of a drug to which the patient had previously become habituated, for example). Likewise, the delivery of one or more thermal waveforms to the vestibular system and/or the nervous system of a patient may enhance the effectiveness of counseling or psychotherapy. In some embodiments, delivery of one or more thermal waveforms to the vestibular system and/or the nervous system of a patient may reduce or eliminate the need for one or more active agents and/or therapies. Adjuvant treatments may be effectuated by delivering one or more thermal waveforms to the vestibular system and/or the nervous system of a patient prior to, currently with and/or after administration of one or more active agents and/or therapies.

"Chronic treatment," "Chronically treating," or the like refers to a therapeutic treatment carried out at least 2 to 3 times a week (or in some embodiments at least daily) over an extended period of time (typically at least one to two weeks, and in some embodiments at least one to two months), for as long as required to achieve and/or maintain therapeutic efficacy for the particular condition or disorder for which the treatment is carried out.

"Waveform" or "waveform stimulus" as used herein refers to the thermal stimulus (heating, cooling) delivered to the ear canal of a subject through a suitable apparatus to carry out the methods described herein. "Waveform" is not to be confused with "frequency," the latter term concerning the rate of delivery of a particular waveform. The term "waveform" is used herein to refer to one complete cycle thereof, unless additional cycles (of the same, or different, waveform) are indicated. As discussed further below, time-varying waveforms may be preferred over constant temperature applications in carrying out the present invention.

"Actively controlled waveform" or "actively controlled time-varying waveform" as used herein refers to a waveform stimulus in which the intensity of the stimulus or temperature of the earpiece delivering that stimulus, is repeatedly adjusted, or substantially continuously adjusted or driven, throughout the treatment session, typically by control circuitry or a controller in response to active feedback from a suitably situated temperature sensor (e.g., a temperature sensor mounted on the earpiece being driven by a thermoelectric device), so that drift of the thermal stimulus from that which is intended for delivery which would otherwise occur due to patient contact is minimized In general, a waveform stimulus used to carry out the present invention comprises a leading edge, a peak, and a trailing edge. If a first waveform stimulus is followed by a second waveform stimulus, then the minimal stimulus point therebetween is referred to as a trough.

The first waveform of a treatment session is initiated at a start point, which start point may be the at or about the subject's body temperature at the time the treatment session is initiated (typically a range of about 34 to 38 degrees Centigrade, around a normal body temperature of about 37 degrees Centigrade. The lower point, 34, is due to the coolness of the ear canal. It typically will not be above about 37 unless the patient is febrile). Note that, while the subject's ear canal may be slightly less than body temperature (e.g., about 34 to 36 degrees Centigrade), the starting temperature for the waveform is typically body temperature (the temp of the inner ear), or about 37 degrees Centigrade. In some embodiments, however, the temperature of the treatment device may not have equilibrated with the ear canal prior to the start of the treatment session, and in such case the start point for at least the first waveform stimulus may be at a value closer to room temperature (about 23 to 26 degrees Centigrade).

The waveform leading edge is preferably ramped or time-varying: that is, the amplitude of the waveform increases through a plurality of different temperature points over time (e.g., at least 5, 10, or 15 or more distinct temperature points, and in some embodiments at least 50, 100, or 150 or more distinct temperature points, from start to peak). The shape of the leading edge may be a linear ramp, a curved ramp (e.g., convex or concave; logarithmic or exponential), or a combination thereof. A vertical cut may be included in the waveform leading edge, so long as the remaining portion of the leading edge progresses through a plurality of different temperature points over time as noted above.

The peak of the waveform represents the amplitude of the waveform as compared to the subject's body temperature. In general, an amplitude of at least 5 or 7 degrees Centigrade is preferred for both heating and cooling waveform stimulation. In general, an amplitude of up to 20 degrees Centigrade is preferred for cooling waveform stimulation. In general, an amplitude of up to 8 or 10 degrees Centigrade is preferred for heating waveform stimulus. The peak of the waveform may be truncated (that is, the waveform may reach an extended temperature plateau), so long as the desired characteristics of the leading edge, and preferably trailing edge, are retained. For heating waveforms, truncated peaks of long duration (that is, maximum heat for a long duration) are less preferred, particularly at higher heats, due to potential burning sensation. In some embodiments, the temperature applied in the ear canal is between about 13° C. and 43° C. The temperature applied in the ear canal range from about 22-24° C. below body temperature to about 6-10° C. above body temperature.

The waveform trailing edge is preferably ramped or time-varying: that is, the amplitude of the waveform decreases through a plurality of different temperature points over time (e.g., at least 5, 10, or 15 or more distinct temperature points, or in some embodiments at least 50, 100, or 150 or more distinct temperature points, from peak to trough). The shape of the trailing edge may be a linear ramp, a curved ramp (e.g., convex or concave; logarithmic or exponential), or a combination thereof. A vertical cut may again be included in the waveform trailing edge, so long as the remaining portion of the trailing edge progresses through a plurality of different temperature points over time as noted above.

The duration of the waveform stimulus (or the frequency of that waveform stimulus) is the time from the onset of the leading edge to either the conclusion of the trailing edge or (in the case of a vertically cut waveform followed by a subsequent waveform). In general, each waveform stimulus has a duration, or frequency, of from one or two minutes up to ten or twenty minutes.

A treatment session may have a total duration of five or ten minutes, up to 20 or 40 minutes or more, depending on factors such as the specific waveform or waveforms delivered, the patient, the condition being treated, etc. For example, in some embodiments a treatment session may be 60 minutes or more. In some embodiments, treatment sessions may include breaks between stimulation, such as breaks of a minute or more.

In a treatment session, a plurality of waveforms may be delivered in sequence. In general, a treatment session will comprise 1, 2 or 3 waveforms, up to about 10 or 20 or more waveforms delivered sequentially. Each individual waveform may be the same, or different, from the other. When a waveform is followed by a subsequent waveform, the minimum stimulus point (minimum heating or cooling) between is referred to as the trough. Like a peak, the trough may be truncated, so long as the desired characteristics of the trailing edge, and the following next leading edge, are retained. While the trough may represent a return to the subject's current body temperature, in some embodiments minor thermal stimulation (cooling or heating; e.g., by 1 or 2 degrees up to 4 or 5 degrees Centigrade) may continue to be applied at the trough (or through a truncated trough).

Treatment sessions are preferably once a day, though in some embodiments more frequent treatment sessions (e.g. two or three times a day) may be employed. Day-to-day treatments may be by any suitable schedule: every day; every other day; twice a week; as needed by the subject, etc. The overall pattern of treatment is thus typically chronic (in contrast to "acute," as used in one-time experimental studies).

Subjects may be treated with the present invention for any reason. In some embodiments, disorders for which treatment may be carried out include, include, but are not limited to, migraine headaches (acute and chronic), depression, anxiety (e.g. as experienced in post-traumatic stress disorder ("PTSD") or other anxiety disorders), spatial neglect, Parkinson's disease, seizures (e.g., epileptic seizures), diabetes (e.g., type II diabetes), etc.

Headaches that may be treated by the methods and apparatuses of the present invention include, but are not limited to, primary headaches (e.g., migraine headaches, tension-type headaches, trigeminal autonomic cephalagias and other primary headaches, such as cough headaches and exertional headaches) and secondary headaches. See, e.g., International Headache Society Classification ICHD-II.

Migraine headaches that may be treated by the methods and apparatuses of the present invention may be acute/chronic and unilateral/bilateral. The migraine headache may be of any type, including, but not limited to, migraine with aura, migraine without aura, hemiplegic migraine, opthalmoplegic migraine, retinal migraine, basilar artery migraine, abdominal migraine, vestibular migraine and probable migraine. As used herein, the term "vesibular migraine"

refers to migraine with associated vestibular symptoms, including, but not limited to, head motion intolerance, unsteadiness, dizziness and vertigo. Vestibular migraine includes, but is not limited to, those conditions sometimes referred to as vertigo with migraine, migraine-associated dizziness, migraine-related vestibulopathy, migrainous vertigo and migraine-related vertigo. See, e.g., Teggi et al., HEADACHE 49:435-444 (2009).

Tension-type headaches that may be treated by the methods and apparatuses of the present invention, include, but are not limited to, infrequent episodic tension-type headaches, frequent episodic tension-type headaches, chronic tension-type headache and probable tension-type headache.

Trigeminal autonomic cephalagias that may be treated by the methods and apparatuses of the present invention, include, but are not limited to, cluster headaches, paroxysmal hemicranias, short-lasting unilateral neuralgiform headache attacks with conjunctival injection and tearing and probable trigeminal autonomic cephalagias. Cluster headache, sometimes referred to as "suicide headache," is considered different from migraine headache. Cluster headache is a neurological disease that involves, as its most prominent feature, an immense degree of pain. "Cluster" refers to the tendency of these headaches to occur periodically, with active periods interrupted by spontaneous remissions. The cause of the disease is currently unknown. Cluster headaches affect approximately 0.1% of the population, and men are more commonly affected than women (in contrast to migraine headache, where women are more commonly affected than men).

Other primary headaches that may be treated by the methods and apparatuses of the present invention, include, but are not limited to, primary cough headache, primary exertional headache, primary headache associated with sexual activity, hypnic headache, primary thunderclap headache, hemicranias continua and new daily-persistent headache.

Additional disorders and conditions that can be treated by the methods and systems of the present invention include, but are not limited to, neuropathic pain (e.g., migraine headaches), tinnitus, brain injury (acute brain injury, excitotoxic brain injury, traumatic brain injury, etc.), spinal cord injury, body image or integrity disorders (e.g., spatial neglect), visual intrusive imagery, neuropsychiatric disorders (e.g. depression), bipolar disorder, neurodegenerative disorders (e.g. Parkinson's disease), asthma, dementia, insomnia, stroke, cellular ischemia, metabolic disorders, (e.g., diabetes), post-traumatic stress disorder ("PTSD"), addictive disorders, sensory disorders, motor disorders, and cognitive disorders.

Sensory disorders that may be treated by the methods and apparatuses of the present invention include, but are not limited to, vertigo, dizziness, seasickness, travel sickness cybersickness, sensory processing disorder, hyperacusis, fibromyalgia, neuropathic pain (including, but not limited to, complex regional pain syndrome, phantom limb pain, thalamic pain syndrome, craniofacial pain, cranial neuropathy, autonomic neuropathy, and peripheral neuropathy (including, but not limited to, entrapment-, heredity-, acute inflammatory-, diabetes-, alcoholism-, industrial toxin-, Leprosy-, Epstein Barr Virus-, liver disease-, ischemia-, and drug-induced neuropathy)), numbness, hemianesthesia, and nerve/root plexus disorders (including, but not limited to, traumatic radiculopathies, neoplastic radiculopathies, vaculitis, and radiation plexopathy).

Motor disorders that may be treated by the method and apparatuses of the present invention include, but are not limited to, upper motor neuron disorders such as spastic paraplegia, lower motor neuron disorders such as spinal muscular atrophy and bulbar palsy, combined upper and lower motor neuron syndromes such as familial amyotrophic lateral sclerosis and primary lateral sclerosis, and movement disorders (including, but not limited to, Parkinson's disease, tremor, dystonia, Tourette Syndrome, myoclonus, chorea, nystagmus, spasticity, agraphia, dysgraphia, alien limb syndrome, and drug-induced movement disorders).

Cognitive disorders that may be treated by the method and apparatuses of the present invention include, but are not limited to, schizophrenia, addiction, anxiety disorders, depression, bipolar disorder, dementia, insomnia, narcolepsy, autism, Alzheimer's disease, anomia, aphasia, dysphasia, parosmia, spatial neglect, attention deficit hyperactivity disorder, obsessive compulsive disorder, eating disorders, body image disorders, body integrity disorders, post-traumatic stress disorder, intrusive imagery disorders, and mutism.

Metabolic disorders that may be treated by the present invention include diabetes (particularly type II diabetes), hypertension, obesity, etc.

Addiction, addictive disorders, or addictive behavior that may be treated by the present invention includes, but is not limited to, alcohol addiction, tobacco or nicotine addiction (e.g., using the present invention as a smoking cessation aid), drug addictions (e.g., opiates, oxycontin, amphetamines, etc.), food addictions (compulsive eating disorders), etc.

In some embodiments, the subject has two or more of the above conditions, and both conditions are treated concurrently with the methods and systems of the invention. For example, a subject with both depression and anxiety (e.g., PTSD) can be treated for both, concurrently, with the methods and systems of the present invention.

The methods and systems according to embodiments of the present invention utilize thermoelectric devices (TEDs) to induce physiological and/or psychological responses in a subject for medically diagnostic and/or therapeutic purposes. Subjects to be treated and/or stimulated with the methods, devices and systems of the present invention include both human subjects and animal subjects. In particular, embodiments of the present invention may be used to diagnose and/or treat mammalian subjects such as cats, dogs, monkeys, etc. for medical research or veterinary purposes.

As noted above, embodiments according to the present invention utilize TEDs to provide an in-ear stimulator for administering thermal stimulation in the ear canal of the subject. The ear canal serves as a useful conduit to the individual's vestibular system and to the vestibulocochlear nerve. Without wishing to be bound by any particular theory, it is believed that thermal stimulation of the vestibular system is translated into electrical stimulation within the central nervous system ("CNS") and propagated throughout the brain, including but not limited to the brain stem, resulting in certain physiological changes that may be useful in treating various disease states (increased blood flow, generation of neurotransmitters, etc). See, e.g., Zhang, et al. *Chinese Medical J.* 121:12:1120 (2008) (demonstrating increased ascorbic acid concentration in response to cold water CVS).

System

Figure 2:
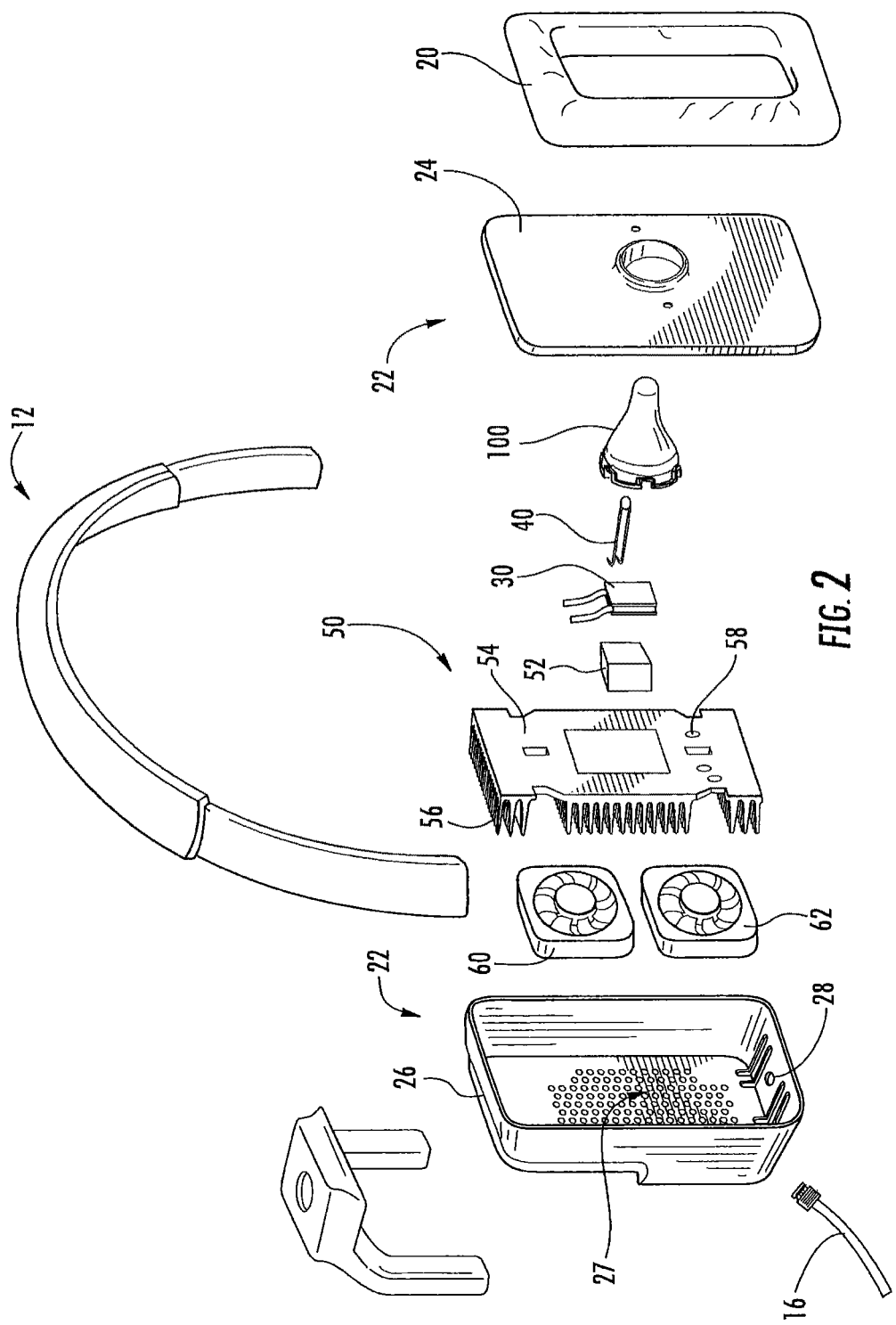
FIG. 2 is an exploded view of the bilateral caloric vestibular stimulation device of FIG. 1.

As illustrated in FIG. 1-2, an in-ear stimulation apparatus 10 includes a support or headband 12, earphones 14 and a controller and/or power connection or cable 16. The earphones 14 include respective earpieces 100 that are configured to be positioned in the ear of a patient or subject. As illustrated in FIG. 2, the earphones 14 include a cushion 20 connected a housing 22 having housing members 24 and 26, the earpiece 100, a thermoelectric (TED) device 30, a temperature sensor 40, a heat sink 50 with a heat sink spacer 52 and a heat sink base 54 with heat dissipating fins 56 and apertures 58, and two air flow devices or fans 60 and 62. The housing 22 includes ventilation apertures 27 for increasing air flow, e.g., via the fans 60, 62 for increasing dissipation of thermal energy. The housing 22 also includes cable apertures 28 for holding electrical connections to the cable 16 such as a power and/or communication cable that controls operations of the fans 60, 62, the TED 30, and/or the temperature sensor 40. The electrical connections (not shown) may further pass through the apertures 58 in the heat sink base to connect with the TED 30 and/or temperature sensor 40.

As illustrated, the temperature sensor 40 may be inserted into a cavity or void in the earpiece 100. However, the temperature sensor 40 may be positioned in any suitable position to sense a temperature of the earpiece 100. As shown in FIG. 6E, the temperature sensor 40 may be inserted into a cavity 102.

The TED 30 is thermally coupled between the earpiece 100 and the heat sink 50 as illustrated in FIG. 2. Although the device 10 is illustrated with one TED 30 in FIG. 2, it should be understood that, in some embodiments, two or more TEDs may be used. In some embodiments, the TEDs are impregnated with and/or connect to the earpiece 100 and heat sink 50 with epoxy to increase a thermal conductivity between the TEDs, the earpiece 100 and/or the heat sink 50. Thus, the TEDs between the earpiece 100 and the heat sink 50 create a temperature difference between the earpiece 100 and the heat sink 50 when a voltage is applied to the TEDs so that the temperature of the earpiece 100 may be increase and/or decreased. The TEDs may be controlled by a controller 200, and the efficiency with which the temperature of the earpiece 100 is changed may be increased by the heat sink 50, which dissipates excess heat or cold from the side of the TEDs opposite the earpiece 100 into the surrounding environment. The heat sink 50 may be passively cooled or actively cooled, for example, by using a fan or other cooling system to further increase heat dissipation. As discussed above, the ear canal may serve as a useful conduit to the subject's vestibular system and/or to the vestibulocochlear nerve for thermal stimulation for providing caloric vestibular stimulation (CVS) and/or cranial nerve stimulation. In some embodiments, commercially available heat sinks may be used, such as from Wakefield Thermal Solutions, Inc., Pelham, N.H., U.S.A. (e.g., Part Number: 609-50AB).

In some embodiments, the slew rate for the earpieces 100 is about 15° C./minute or greater for cooling the earpiece 100 and 20° C./minute or greater for heating the earpiece 100. Heating the earpiece may be faster and more efficient than cooling.

Thin film TEDs, Peltier coolers/heaters or transducers may be used as transducers in some embodiments, including, but not limited to, the thin film TEDs described in U.S. Pat. No. 6,300,150 and U.S. Patent Publication Nos. 2007/0028956 and 2006/0086118; however, any suitable TED, such as semiconductor diode TED's, may be used. Such TEDs may also incorporate a temperature sensing function, so that temperature sensing can be accomplished through the same device without the need for a separate temperature sensor. In some embodiments, the temperature sensor 40 may be a thermistor or other temperature sensing element that is disposed in the distal end of the earpiece and used as a feedback sensor to allow the controller 200 to maintain the proper temperature for a given thermal waveform. TEDs are commercially available from TE Technology, Inc, (Traverse City, Mich., USA), Nextreme Thermal Solultions (Durham, N.C., USA)(e.g., OptoCooler™ Series (UPT40 and UPF4), Eteg™ UPF40) and Micropelt, GmbH (Freiburg, Germany) (e.g., MPC-D303 and MPC-D305). Although embodiments according to the invention are described herein with respect to TEDs, it should be understood that any suitable type of thermal device may be used, including optical heating (e.g., using a laser) and ultrasound heating (e.g., a piezoelectric heating device). TEDs may be provided that include a heat flux of 80-120 W/cm$^2$ or more. The TEDs may be generally rectangular in shape, with typical rectangular areas being about 2×1 mm or 5×2 mm or more and having a height profile of 1 mm or 0.65 mm or 0.5 mm or less. In particular embodiments, the TED is about a rectangular shape having sides of about 12-13 mm and a height profile of about 3 mm. When more than one TED is used, the TEDs may be connected in parallel or in series to provide thermal changes to a desired region of an earpiece and/or heat sink.

In some embodiments, the cushion 20 and/or heat sink spacer 52 may be sized and/or configured to increase comfort and/or the fit of the earpiece 100 in the subject's ear canal. The cushion 20 and/or spacer 52 may be sized or may be adjustable so as to place the earpiece 100 in the ear canal with sufficient thermal contact, but without placing excessive pressure on the ear canal. In some embodiments, the controller 200 controls operation of the TED 30 via additional electrical connections/controllers, such as a PCB (not shown), which may be electrically connected to the TED 30 either via cables or between the earpiece 100 and the heat sink 50 and may provide a power supply and control signals for operating the TEDs, such as control signals to control desired temperatures and temperature changes, from the controller. The controller 200 receives feedback from the temperature sensor 40 in the distal end of the earpiece that may properly modulate the power applied to the TED so as to generate the desired thermal waveform. In addition, the cable 16 may include an electrical connection between the two earpieces 100 that may be used to provide an impedance measurement to estimate a degree of electrical and thermal contact between the earpieces. The earpiece 100 may further include a temperature sensor/controller so that the TEDs may provide a temperature stability, e.g., of about 0.1-0.5° C. Although some embodiments for providing an impedance measurement are described herein with respect to an electrical connection between two earpieces, it should be understood that an impedance measurement may be taken from a single earpiece that is electrically connected to a conductive member positioned on the user, such as an electrode attached to the user and spaced apart from the earpiece, to provide impedance measurements that may be used to estimate a degree of thermal contact between the earpiece and the ear canal as described herein.

It should be understood that other configurations for supporting the headphones and/or earpieces may be used, including support bands that are positioned under the chin or over the ear, for example, as may be used with audio earphones. For example, FIG. 3 illustrates four straps or headbands 12' and earphones 14'. The headbands 12' may provide increased stability of the earphones 14' to provide potentially improved thermal contact of the earpieces (not shown).

Additional configurations may be used to potentially increase comfort and/or fit of the headset and/or improve a thermal contact between the earpiece 100 and the ear canal.

Figure 4:
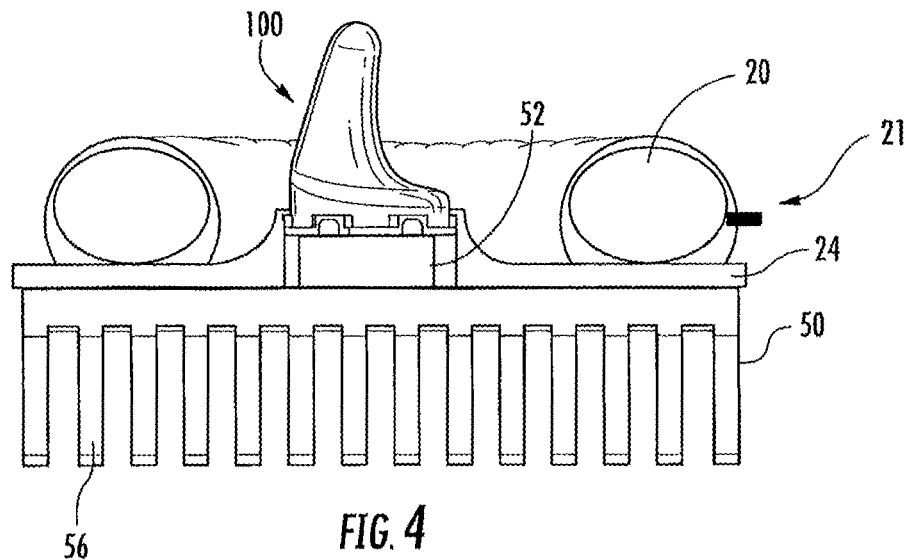
FIG. 4 is a side view of an earpiece with an inflatable cushion according to some embodiments of the present invention.

For example, as shown in FIG. 4, the cushion 20 can include an inlet 21 for inflating an inner chamber of the cushion 20. In this configuration, the distance of the earpiece 100 from the subject's head may be controlled by adjusting an amount of fluid, such as air, that is added into or released from the cushion 20. As the cushion 20 inflates, the earpiece 100 is pushed further away from the subject's head, and when the cushion 20 is deflated, the earpiece 100 may be pressed closer to the subject's head for a tighter fit between the earpiece 100 and the ear canal.

Earpiece

Figure 5:
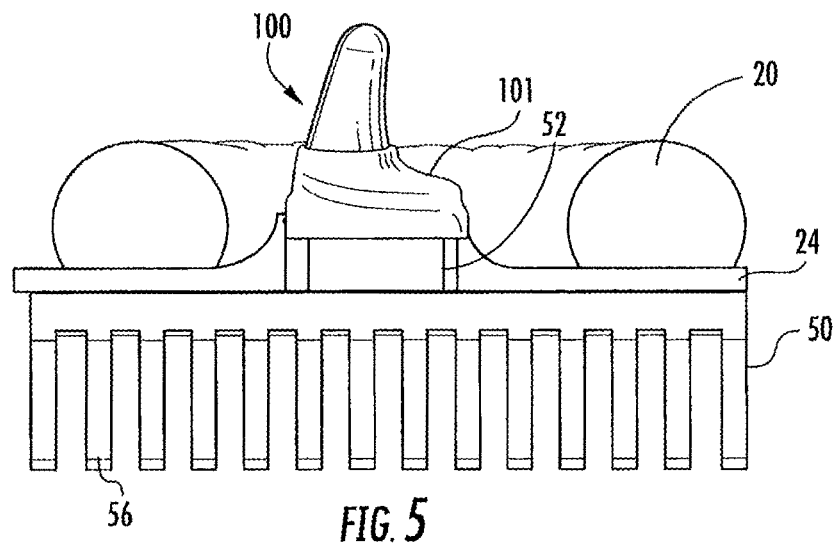
FIG. 5 is a side view of an earpiece with an insulative sleeve according to some embodiments of the present invention.

In some embodiments as shown in FIG. 5, a sheath 101 may be provided to insulate the base portion of the earpiece 100. Without wishing to be bound by theory, is currently believed that changes in temperature of the earpiece should be concentrated at a part of the earpiece 100 that is inserted the deepest into the ear canal for increasing caloric vestibular stimulation. Accordingly, the sheath 101 may reduce a thermal coupling of the base of the earpiece 100 with the subject's ear to provide more efficient heating and cooling to the distal end of the earpiece 100. In addition, the sheath 101 in some embodiments may provide additional cushioning or padding for increased comfort to the user. The sheath 101 may be formed of any suitable material, such as elastomer or polymeric material, medical grade silicone and the like. Moreover, in some embodiments, the earpiece 100 may be covered with a thermally conductive material to increase a thermal contact with the ear canal. In some embodiments, a thermally conductive material may be applied only to the distal end of the earpiece 100; however, any portion of the earpiece 100 may incorporate thermally conductive materials. Any suitable thermally conductive material may be used, including gels, water, water-based lubricants, and the like. In some embodiments, the thermally conductive material is a coating material that is applied and reapplied to the earpiece 100 before each use. In some embodiments, the thermally conductive material may be a sheath or sleeve (e.g., a gel or plastic sleeve) that is fitted to the earpiece during use and may be reusable. Therefore, it should be understood that coatings or sheath materials may be provided to selectively thermally insulate the earpiece 100 or to increase a thermal conductivity between the earpiece 100 and the ear canal.

In some embodiments, the sheath 101 may be a layer (e.g., around 1 mm) that is selectively applied to the base of the earpiece 100 but not the distal tip portion that is inserted into the ear canal. In addition to thermally insulating the base of the earpiece 100, the sheath 101 may also provide a cushion against the inward pressure of the headset, thus enhancing patient comfort during the CVS therapy application. The sheath 101 may also be electrically insulating as well as thermally insulating.

As shown in FIG. 6A, the earpiece 100 may be connected to the heat sink 50 by the TED 30. The heat sink 50 is thermally isolated from the earpiece 100. The TEDs 30 are positioned on a surface 53 of a spacer portion 52 of the heat sink 50 so that thermal coupling between the TED 30 and the earpiece 100 may be achieved. The TEDs 30 are also thermally coupled to the heat sink 50 on a side of the TEDs that are opposite to the earpiece 100 so as to create a thermal differential between the heat sink 50 and the earpiece 100. The TED 30 may be adhered to the earpiece 100 using a thermally conductive adhesive, such as silver. It should be understood that the TED 30 may be thermally connected to the earpiece 100 and heat sink 50 at any suitable location to provide a thermal differential between the heat sink 50 and the earpiece 100.

In some embodiments, the earpiece 100 may be connected to an electrical connection or electrode 45. Although the electrode 45 is illustrated on an outer surface of the earpiece 100, it should be understood that the electrode 45 may be connected to interior surfaces or embedded in the earpiece in any configuration that is suitable to electrically connect the electrode 45 with the earpiece. In this configuration, a relatively small electrical current may be applied via the electrode 45 to both earpieces 100 shown, e.g., in FIG. 1. Without wishing to be bound by theory, it is believed that if generally good thermal contact between the earpiece 100 and the ear canal is achieved, then the patient's body/head will generally complete an electrical circuit between the earpieces 100. Thus, the impedance or other equivalent electrical measurement between the earpieces 100 may be measured to estimate a thermal contact between the earpieces 100 and the ear canal of the patient and/or to measure patient compliance with treatment.

Figure 25:
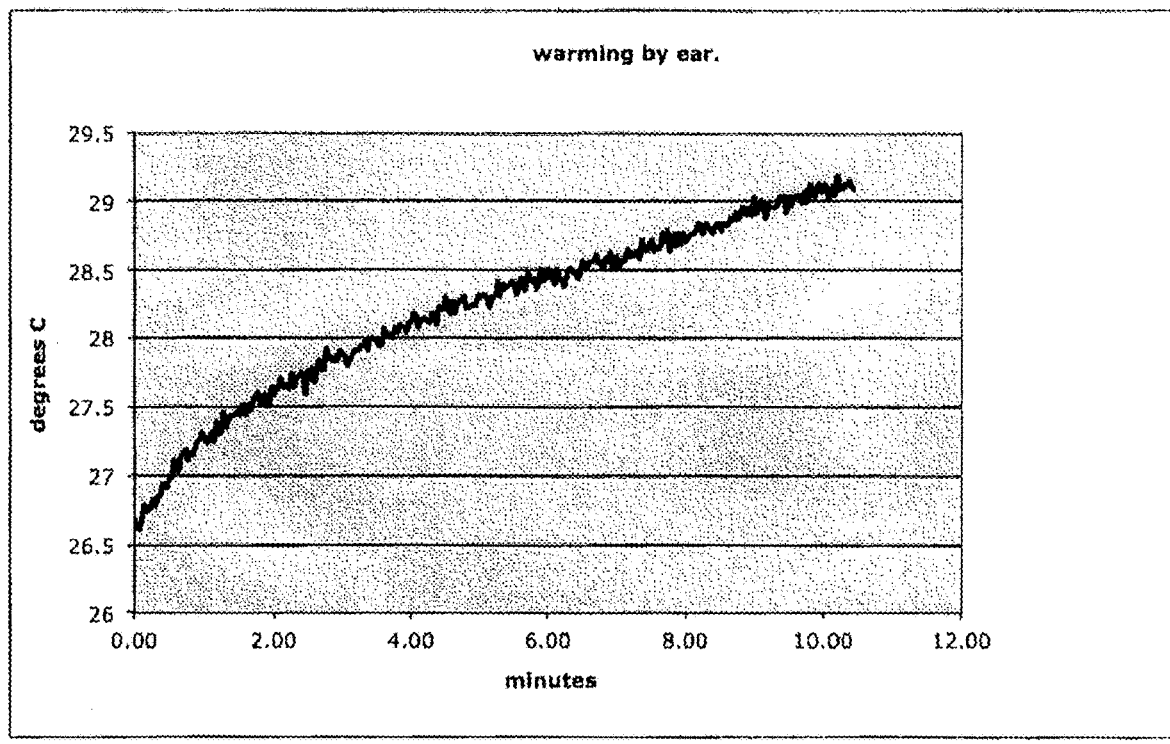
FIG. 25 is a graph of a temperature sensor output as a function of time when an earpiece according to some embodiments is positioned in the ear.

In some embodiments, the temperature output of the temperature sensor 40 may be used to estimate a thermal contact between the earpieces 100 and the ear canal of the patient and/or to measure patient compliance with treatment. For example, as illustrated in FIG. 25, the temperature sensor output as a function of time when an earpiece 100 is positioned in the ear may increase over time until equilibrium is reached. Therefore, an increase in temperature as sensed by the temperature sensor 40 may be used to determine that the earpiece 100 is in position and/or to estimate whether the earpiece 100 has relatively good or relatively poor thermal contact with the ear. A temperature monitor may be used to detect and/or store the temperature output and to determine a degree of thermal contact with the ear canal based on the temperature output.

Figure 26:
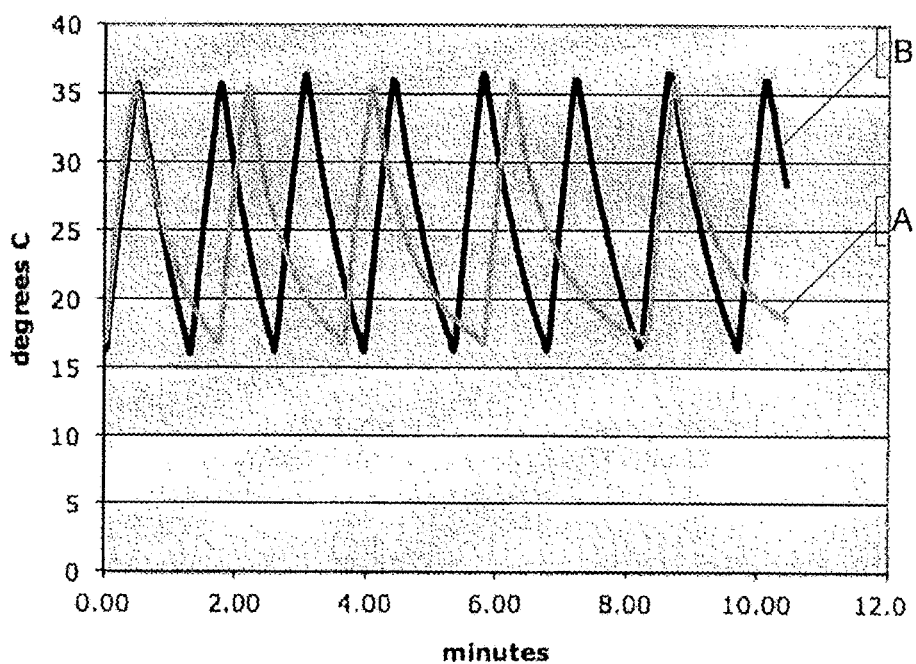
FIG. 26 is a graph of a temperature sensor output as a function of time for a temperature sensor in an earpiece that is positioned in the ear and an earpiece that is not positioned in the ear during the delivery of a time-varying thermal waveform according to some embodiments.

Moreover, the output of the temperature sensor 40 may be used to determine that the earpiece 100 is in position in the ear and/or to estimate whether the earpiece 100 has relatively good or relatively poor thermal contact with the ear. FIG. 26 is a graph of a temperature sensor output as a function of time for a temperature sensor in an earpiece 100 that is positioned in the ear (line A) and an earpiece 100 that is not positioned in the ear (line B) during the delivery of a time-varying thermal waveform according to some embodiments. The earpiece 100 that is in the ear results in a temperature output that illustrates a different shape due to the thermal loading of the ear. In some embodiments, the number of cycles completed during a treatment period may be measured. The number of cycles measured during use in the ear will be smaller than the number of cycles measured when the headset is sitting in air. That is, the human body slows down the ability of the device to complete cycles. In some embodiments, the degree to which the cycles are slowed may be used to determine an amount of thermal contact. For example, good thermal contact between the earpiece 100 and the ear canal may result in fewer cycles or a slowing of cycles as compared with bad thermal contact or no thermal contact. In some embodiments, the control signal from the waveform generator may be compared with the temperature output, and a degree of thermal contact between the earpiece and the ear canal may be determined based on a lag time between the control signal and the temperature output. A longer delay between a temperature driven by the control signal and the temperature output may indicate better thermal contact between the earpiece 100 and the ear canal than a shorter delay or more "real-time" relationship between the control signal and the temperature output.

As shown in FIG. 6B, the TEDs 30 may be disposed between the base of the earpiece 100 and the heat sink 50 and impregnated with epoxy 32. In some embodiments, the epoxy 32 provides structural stability to the earpiece 100, TED 30 and heat sink 50 assembly. However, it should be understood that any suitable configuration may be used, and in some embodiments, the epoxy may be omitted and/or thermally conductive adhesives may be used. Additional configurations of heat sinks, TEDs and earpieces that may be used in some embodiments of the present invention are discussed in U.S. patent application Ser. Nos. 12/970,347 and 12/970,312, filed Dec. 16, 2010, the disclosures of which are hereby incorporated by reference in their entireties. In this configuration, caloric vestibular stimulation may be administered to a subject via the subject's ear canal.

Figure 6C:
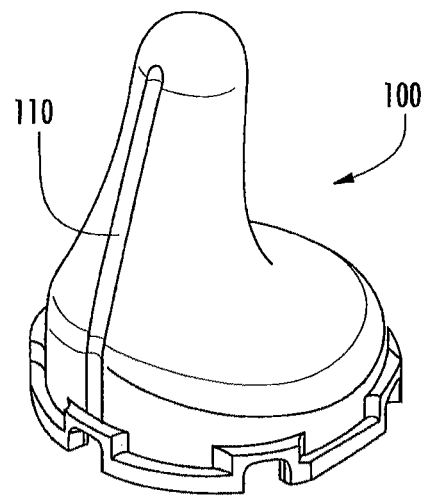
FIGS. 6C-6E are perspective, side and cross-sectional views, respectively, of an earpiece according to some embodiments of the present invention.
Figure 6D:
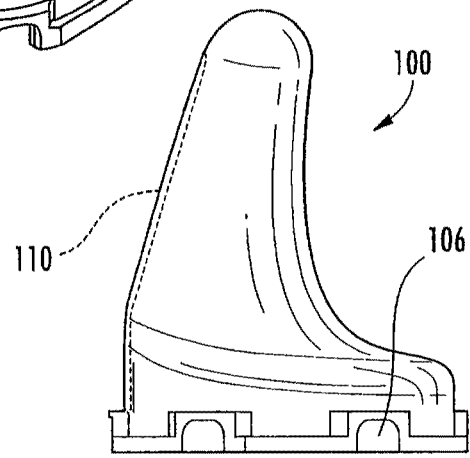
Figure 6E:
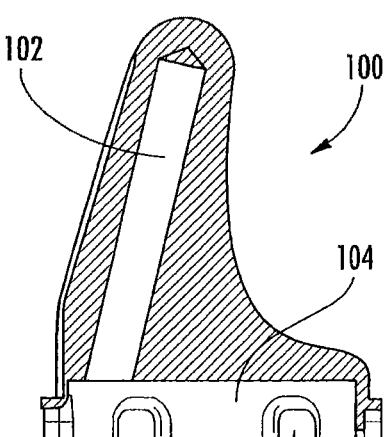

As shown in FIG. 6C-6E, the earpiece 100 includes a tip cavity 102, a base cavity 104, base apertures 106, and an pressure relief channel 110. The tip cavity 102 is configured to receive a thermistor or temperature sensor, such as the temperature sensor 40 so that the temperature of the tip of the earpiece 100 may be monitored. The base cavity 104 is configured to receive the TED 30 such that the TED 30 is mounted on an interior cavity surface of the earpiece 100 on one side, and the TED 30 is mounted on the heat sink 50 on the opposite side as described in FIG. 2. The base apertures 106 are configured to provide a passageway for wires and/or cables to connect a power source and/or control signal to the TED 30 and/or temperature sensor 40 or other sensors and/or monitors that may be used with the earpiece 100.

The pressure relief channel 110 is configured to provide a pathway through which air may flow during and/or after insertion of the earpiece 100 into the ear canal of the patient. Accordingly, the earpiece 100 may be formed of a rigid material, e.g., a metal such as aluminum that has an associated specific heat such that the earpiece may provide a slew rate that is about 15° C./minute or greater for cooling the earpiece 100 and 20° C./minute or greater for heating the earpiece 100. However, the rigid surface of the earpiece 100 may result in a increased pressure during insertion because the generally non-conformable surface of the earpiece 100 may seal air inside the ear canal. Thus, the pressure relief channel 110 may permit additional airflow through the channel 110 to reduce the pressure in the ear canal during and/or after the insertion of the earpiece 100 into the ear canal of the patient. In this configuration, the earpiece comfort and/or fit may be improved to provide a close thermal contact between the generally rigid surface of the earpiece 100 and the ear canal of the patient to increase the efficiency with which the vestibular nerve may be thermally stimulated. The pressure relief channel 110 may be of a length and depth that is sufficient to provide air flow from the interior of the ear canal at the distal tip of the earpiece to the external air outside of the ear canal. For example, the channel 110 may be generally as long as a side of the earpiece 100 and may be between about 0.5 mm and about 2.0 mm deep.

Although the pressure relief channel 110 is illustrated as being on a side of the earpiece 100 that extends nearly vertically away from the base, it should be understood that the pressure relief channel 110 may be positioned on any portion of the outer surface of the earpiece 100. Moreover, in some embodiments, a pressure relief channel may be positioned on an interior portion of the earpiece 100 to provide a conduit between the interior ear canal of the patient and the exterior air.

In some embodiments, the earpiece 100 may be coated to prevent degradation of the surface quality. Depending on the application, the coating may be electrically conductive, electrically non-conductive, or a combination of both. For example, the surface of the earpiece 100 may be anodized such that a non-conductive coating is grown on aluminum using an anodization process. This process creates an aluminum oxide coating that renders the surface electrically insulting. The coating is very thin, however, and there is little if any degradation of the thermal conductivity. Colorants may be added during the anodization for a visually enhanced appearance. The aluminum may also be coated with an electrically conductive material, which can be applied by painting, dipping, spraying, etc. Such a coating may also prevent surface degradation by keeping the underlying aluminum from being exposed to air. The layer can be applied so as to have a minimal change or no change in the degradation of thermal conductivity. In particular embodiments, the earpiece 100 may be patterned with more than one coating, using techniques common in the art, so that both electrically conductive and non-conductive coatings may coexist on the earpiece.

In some embodiments, impedance may be measured using the electrode 45 in FIG. 6A. Impedance is a complex quantity (that is, having both real and imaginary parts) that may combine both resistive (real) and capacitive (imaginary) components, and impedance may be measured with an alternating current/voltage method. The capacitance may be measured with electrically insulated earpieces (e.g., anodized), but electrically insulated earpieces would generally not permit a measurement of resistance, which would typically require electrical contact between the earpiece 100 and the ear canal. The earpiece 100 may be patterned with electrically insulating and electrically conductive portions so that the base is anodized and the distal tip has a conductive coating. This would allow both resistance and capacitance to be measured (or the entire earpiece could be coated with an electrically conductive material). In summary, either coating type could be used to measure an impedance value for estimating a thermal conductivity.

Although embodiments according to the present invention are described herein with respect to a device with two earpieces (see, e.g., the earpieces 100A, 100B in FIG. 8), it should be understood that in some embodiments, a single earpiece may be used to deliver thermal vestibular stimulation to one ear canal of a patient. A single earpiece caloric vestibular stimulation device may utilize a single earpiece having various combinations of the features described herein.

Controllers

Figure 7:
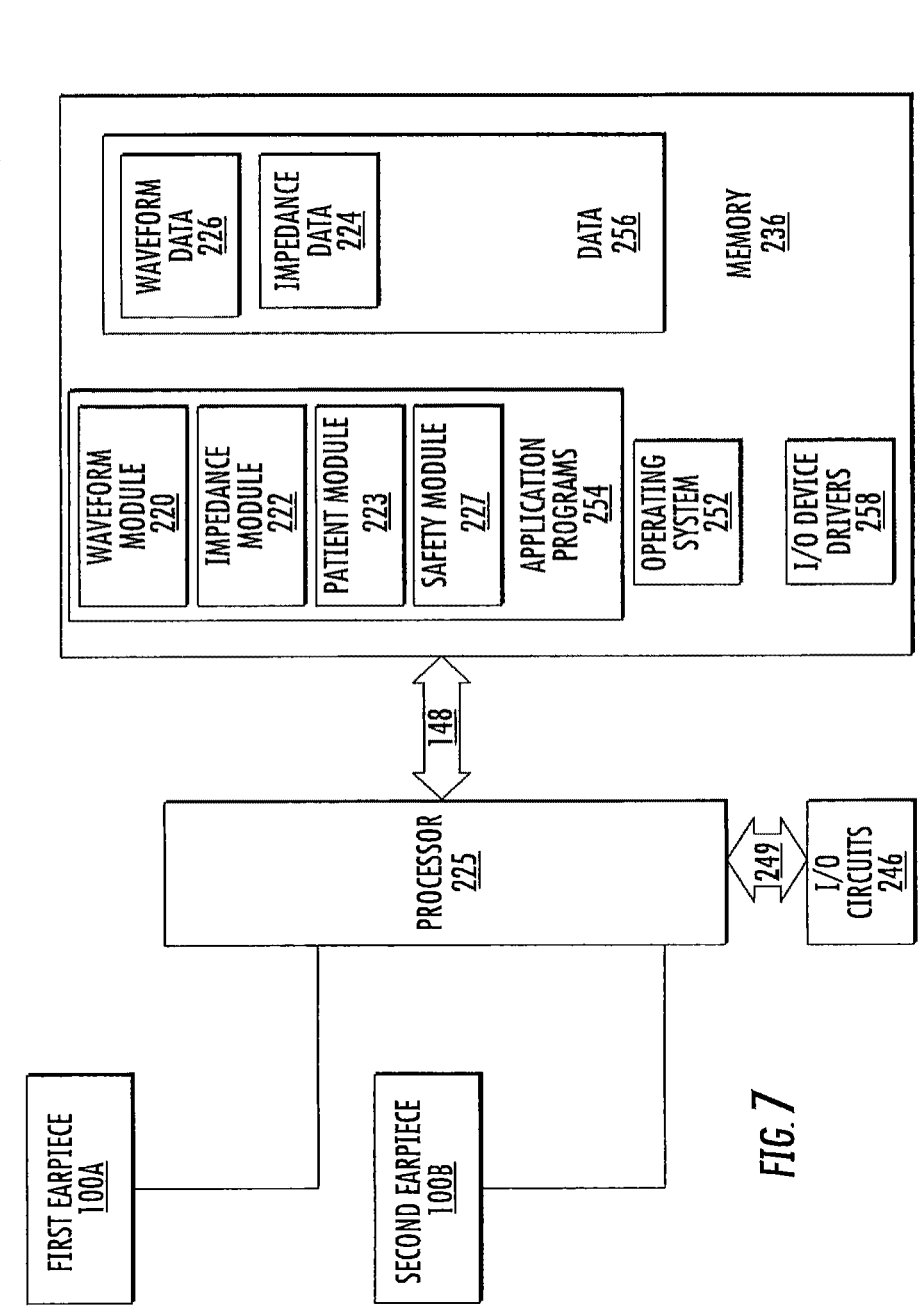
FIG. 7 is a schematic diagram of a bilateral caloric vestibular stimulation system according to some embodiments of the present invention.

FIG. 7 is a block diagram of exemplary embodiments of controller systems 200 of the present invention for controlling a thermal output to two earpieces 100A, 100B to administer various thermal treatment protocols or thermal "prescriptions." As shown in FIG. 7, in some embodiments, the controller 200 includes a memory 236, a processor 225 and I/O circuits 246 and is operatively and communicatively coupled to the earpieces 100A, 100B. The processor 225 communicates with the memory 236 via an address/data bus 248 and with the I/O circuits via an address/data bus 249. As will be appreciated by one of skill in the art, the processor 225 may be any commercially available or custom microprocessor. The memory 236 is representative of the overall hierarchy of memory devices containing software and data used to implement the functionality of the controller 200. Memory 236 may include, but is not limited to, the following types of devices: cache, ROM, PROM, EPROM, EEPROM, flash memory, SRAM and DRAM.

As shown in FIG. 7, the controller memory 236 may comprise several categories of software and data: an operating system 252, applications 254, data 256 and input/output (I/O) device drivers 258.

As will be appreciated by one of skill in the art, the controller may use any suitable operating system 252, including, but not limited to, OS/2, AIX, OS/390 or System390 from International Business Machines Corp. (Armonk, N.Y.), Window CE, Windows NT, Windows2003, Windows2007 or Windows Vista from Microsoft Corp. (Redmond, Wash.), Mac OS from Apple, Inc. (Cupertino, Calif.), Unix, Linux or Android.

The applications 254 may include one or more programs configured to implement one or more of the various operations and features according to embodiments of the present invention. The applications 254 may include a thermal waveform control module 220 configured to communicate a waveform control signal to one or both of the TED's of the earpieces 100A, 100B. The applications 254 may also include an impedance module 222 for measuring an impedance or other analogous electrical characteristic (e.g., capacitance) between the earpieces 100A, 100B, a patient module 223 for monitoring patient-specific data, such as compliance and/or a safety monitoring module 227. In some embodiments, the memory 236 comprises additional applications, such as a networking module for connecting to a network, for example, as discussed in U.S. Provisional Application Ser. No. 61/424,474 filed Dec. 17, 2010, the disclosure of which is incorporated by reference in its entirety. In some embodiments, the waveform module 220 may be configured to activate at least one TED (i.e., to control the magnitude, duration, waveform and other attributes of stimulation delivered by the at least one TED). In some such embodiments, the control module 220 is configured to activate at least one TED based upon a prescription from a prescription database, which may include one or more sets of instructions for delivering one or more time-varying thermal waveforms to the vestibular system of a subject as described in U.S. Provisional Application Ser. No. 61/424,474 filed Dec. 17, 2010. In some such embodiments, the waveform module 220 is configured to selectively and separately activate a plurality of TEDs (e.g., by activating only one of the plurality of TEDs, by heating one TED and cooling another, by sequentially activating the TEDs, by activating different TEDs using different temperature/timing parameters, combinations of some or all of the foregoing, etc.).

The data 256 may comprise static and/or dynamic data used by the operating system 252, applications 254, I/O device drivers 258 and other software components. The data 256 may include a thermal waveform database 226 including one or more thermal treatment protocols or prescriptions. In some embodiments, the data 256 further includes impedance data 224 including impedance measurements between the earpieces and/or estimates of thermal contact based on electrical impedance measurements. Electrical impedance measurements may include resistive and capacitive components, which may be correlated with a thermal impedance or thermal conductance of the interface between the earpieces 100A, 100B and the ear canal. In some embodiments, the memory 236 includes additional data, such as data associated with the delivery of one or more time-varying thermal waveforms, including patient outcomes, temperature measurements of the ear as a result of the thermal stimulation, and the like.

I/O device drivers 258 typically comprise software routines accessed through the operating system 252 by the applications 254 to communicate with devices such as I/O ports, memory 236 components and/or the TED device 30.

In some embodiments, the TED thermal waveform control module 220 is configured to activate at least one TED in the earpieces 100A, 100B to stimulate the nervous system and/or the vestibular system of a subject. In particular embodiments, the TED thermal control waveform module 220 is configured to activate at least one TED based upon a thermal prescription comprising a set of instructions for delivering one or more time-varying thermal waveforms to the vestibular system of a subject.

In some embodiments, the controller 200 is communicatively connected to at least one TED in the earpiece 100 via a thermal stimulation conductive line. In some embodiments, the controller 200 is operatively connected to a plurality of TEDs, and the controller 200 may be operatively connected to each TED via a separate thermal stimulation conductive line. In some such embodiments, each of the plurality of separate thermal stimulation conductive lines is bundled together into one or more leads (e.g., the thermal stimulation conductive lines connected to the TED(s) thermally coupled to the right earpiece may be bundled separately from the thermal stimulation conductive lines connected to the TED(s) thermally coupled to the left earpiece). In some such embodiments, the thermal stimulation conductive lines are connected to the controller 200 via a lead interface (e.g., one or more leads may be connected to the controller 200 using an 18-pin connector).

In some embodiments, the controller 200 is operatively connected to at least one TED in the earpieces 100A, 100B via an electrical stimulation conductive line. In some embodiments, the controller 200 is operatively connected to a plurality of TEDs, and the controller may be operatively connected to each TED via a separate electrical stimulation conductive line. In some such embodiments, each of the plurality of separate electrical stimulation conductive lines is bundled together into one or more leads (e.g., two leads, with the conductive lines connected to the TEDs in the right ear being bundled separately from the conductive lines connected to the TEDs in the left ear). In some such embodiments, the electrical stimulation conductive lines are connected to the controller via a lead interface (e.g., two leads may be plugged into the controller using a shared 18-pin connector).

In some embodiments, the controller 200 is operatively connected to at least one TED in the earpieces 100A, 100B via a wireless connection, such as a Bluetooth connection. In some embodiments, the controller 200 is configured to activate the TED 30 to deliver one or more actively controlled, time-varying thermal waveforms to the vestibular system and/or the nervous system of a patient.

In some embodiments, the impedance module 222 is configured to detect and/or monitor an impedance between the two earpieces 100A, 100B. For example, as illustrated in FIG. 8, an electrical connector 221 is used to electrically connect the two earpieces 100A, 100B. the electrical connector 221 may be any electrically conductive material, such as a metal wire that may be physically connected to the earpieces 100A, 100B and connected through, for example, the cable 16 and/or controller 200 as illustrated in FIG. 1.

In some embodiments, the patient module 223 is configured to analyze patient-specific parameters and/or data. For example, the patient module 223 may combine data from the waveform module 220 and the impedance module 222 to determine if the patient has complied with a treatment plan based on whether the impedance values are consistent with the earpieces 100A, 100B being correctly positioned during administration of the treatment. In some embodiments, the patient module 223 may be used to enter and record patient diary information, such as pain scores, occurrences of a conditions (e.g., a headache), additional treatments that are being administered, and the like.

Figure 8:
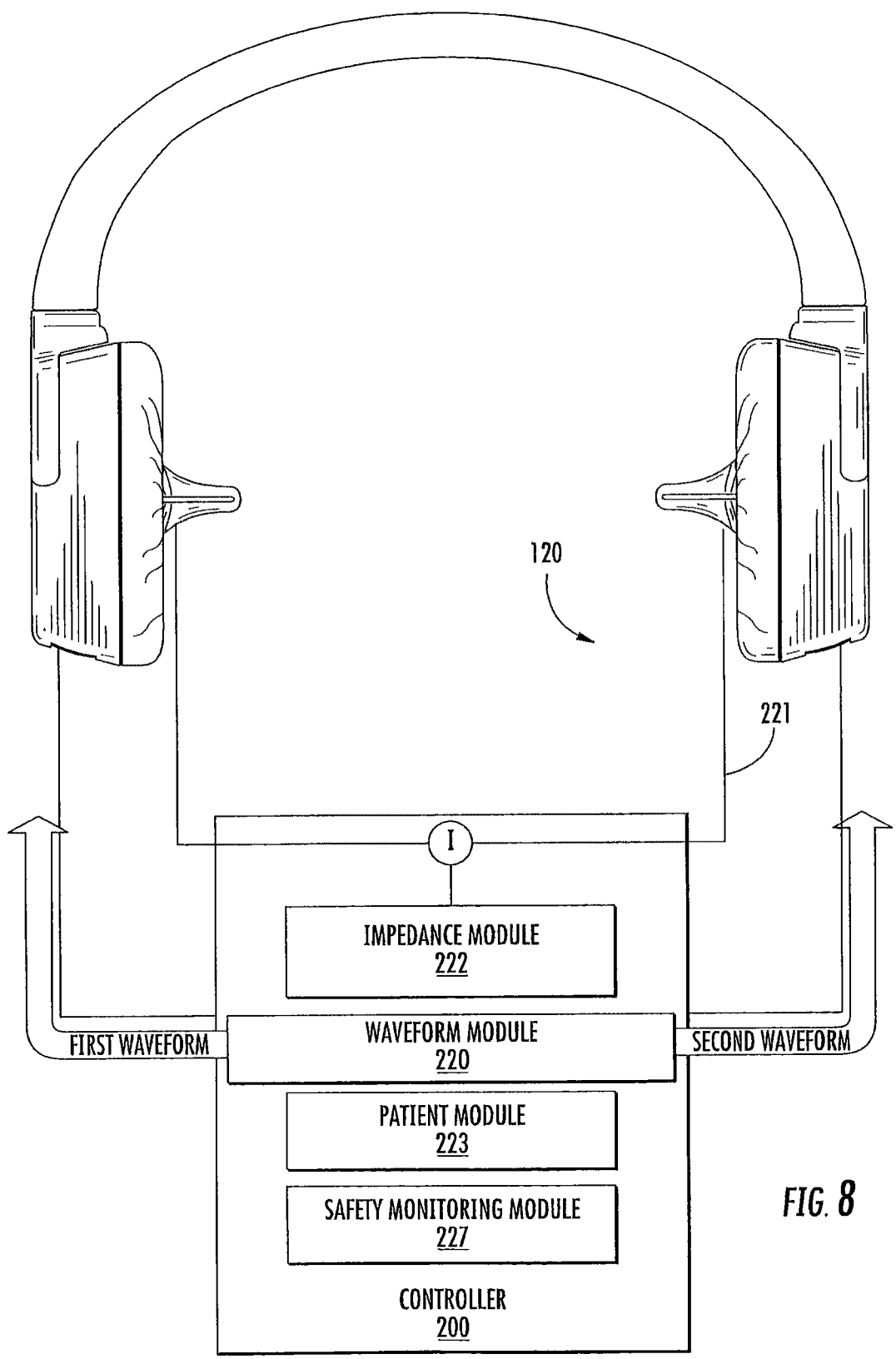
FIG. 8 is a schematic diagram of the controller and earpieces of the bilateral thermal stimulation system of FIG. 7.

As illustrated in FIG. 8, the impedance module 222 may deliver an electrical current via the electrical connector 221 to one of the earpieces 100A, 100B. Again without wishing to be bound by theory, it is believed that if the earpieces 100A, 100B are in generally good thermal contact with the subject's ear canal, then the earpieces 100A, 100B will also be in substantially good electrical contact with the subject's ear canal and the subject's head will substantially complete an electrical circuit between the earpieces 100A, 100B. However, if the earpieces 100A, 100B are not in good thermal contact with the subject's ear canal, then there will also be poor electrical contact with the subject's ear canal, the subject's head will not complete the electrical circuit between the earpieces 100A, 100B, and an open circuit will be detected by the impedance module 122.

In this configuration, the impedance and/or capacitance value between the earpieces 100A, 100B may be used to estimate the thermal contact between the earpieces 100A, 100B. In some embodiments, impedance and/or capacitance values may be detected for a range of subjects to determine a range of impedance and/or capacitance values in which it may be assumed that the earpieces 100A, 100B are in sufficient thermal contact with the subject's ear canal. When a headset is being fitted to a new patient, the impedance and/or capacitance between the earpieces 100A, 100B may be detected, and if the impedance value is within the acceptable range, it may be assumed that there is good thermal contact between the earpieces 100A, 100B and the subject's ear canal.

In some embodiments, when the headset is being fitted to a new patient, the impedance and/or capacitance value between earpieces 100A, 100B may be detected and used as a patient specific baseline to determine if the patient is later using the headset and a proper configuration. For example, the patient may use a headset according to embodiments of the present invention in a setting that may or may not be supervised by a medical professional. In either environment, the impedance module 222 may record an impedance and/or capacitance value at a time that is close in time or overlapping with the time in which the treatment waveforms are delivered to the earpieces. The medical health professional or the impedance module 222 may analyze the impedance value to determine whether the earpieces 100A, 100B were properly fitting during treatment. In some embodiments, the impedance module 222 may be configured to provide feedback to the user when impedance values detected on the electrical connector 120 that are inconsistent with properly fitting earpieces 100A, 100B in good thermal contact with the ear canal. In this configuration, the impedance module 222 may provide an estimation of a degree of thermal contact between the earpieces 100A, 100B and the ear canal in real-time or in data recorded and analyzed at a later time. Accordingly, patient compliance with treatment protocols may be monitored based on the detected impedance during or close in time to treatment.

In particular embodiments, the impedance module 222 may also provide feedback to the waveform module 220, for example, so that the waveform module 220 may increase or decrease an amplitude of the waveform control signal responsive to the degree of thermal contact determined by the impedance module 222 based on the impedance and/or capacitance value of the electrical connector 221. For example, if the impedance module 222 determines based on the impedance value of the electrical connector 221 that there is a poor fit and poor thermal contact with the ear canal, then the waveform module 220 may increase the thermal output to the earpieces 100A, 100B to compensate for the poor thermal contact. In some embodiments, the impedance module 222 may determine patient compliance, e.g., whether the patient was actually using the device during administration of the waveforms.

Although embodiments of the present invention are illustrated with respect to two earpieces 100A, 100B, it should be understood that in some embodiments, a single earpiece may be used, and an electrical contact may be affixed to another location on the user's head instead of the second earpiece to thereby provide an electrical circuit for determining impedance values and estimating thermal contact as described herein.

As illustrated in FIG. 8, the waveform module 220 may be configured to communicate first and second waveforms to the TEDs 30 of the earpieces 100A, 100B. It should be understood that the first and second waveforms may be the same, or in some embodiments, the first and second waveforms may be different such that the thermal output delivered from the TEDs 30 to the earpieces 100A, 100B are independently controlled and may be different from one another.

The safety monitoring module 227 may receive sensor data from the earpieces 100A, 100B, the heat sinks 50 (FIGS. 1-2), or from various electrical components of the system, including a power output from the waveform module 220. The safety monitoring module 227 is configured to analyze the sensor data or other data such as power output data to determine if elements of the system may be operating outside of a predefined safety range and to disable or cease operation of the waveform module 220 in the event that unsafe parameters are detected. For example, the sensor data may include temperature data from the earpieces 100A, 100B and/or the heat sinks 50 such that if the earpieces 100A, 100B and/or the heat sinks 50 are operating above or below a given temperature (for example, greater than about 50-55° C.), then the safety monitoring module 227 ceases operation of the device, for example, by halting the delivery of different waveforms and/or by driving the earpieces 100A, 100B to a safer temperature. The safety monitoring module 227 may implement safety procedures, such as halting the delivery of different waveforms and/or driving the earpieces 100A, 100B to a safer temperature, if a voltage to drive the TED 30 is above a threshold value, if the safety monitoring module 227 detects that the fans 60, 62 are not properly operating, and/or if other conditions are detected that indicate patient safety issues may occur.

In some embodiments, the power from the waveform module 220 may be delivered to the TED 30 of the earpieces 100A, 100B via a power cable, and sensor data, for example, from the temperature sensor 40 and/or temperature sensors positioned in other suitable locations of the device, such as to measure a temperature of the heat sink 50, may be communicated to the controller 200 via a wireless connection. Such a wireless sensor connection may reduce or eliminate signal interferences between a power cable and the sensor signal over configurations in which the sensor signal would be supplied via the same cable as the power to the TED 30. A wireless sensor signal connection to the control 200 may also reduce a weight of the cable and thus increase patient comfort.

Waveforms

Without wishing to be bound by theory, functional imaging studies may indicate that there is a generally dominant laterality to caloric stimulation. See Marcelli et al., *Spatio-*

*Temporal Pattern of Vestibular Information Processing after Brief Caloric Stimulation*, European Journal of Radiology, vol. 70, 312-316 (2009). Stated otherwise, cold calorics tend to activate contralateral brain regions, and warm calorics tend to activate ipsilateral brain regions. For example, it has been found that short, left ear stimulation lead to right brain activation. See id. Accordingly, it is currently believed that independent dual ear stimulation may allow combinations to target specific regions and/or hemispheres of the brain. For example, and again without wishing to be bound by theory, warm stimulation may increase the phasic firing rate of the afferents of the vestibular system, and cold stimulation may decrease phasic firing rates. Thus, it is currently believed that the laterality of activation for a given temperature above or below body temperature and a sawtooth waveform may cover a spectrum of phasic frequencies for vestibular stimulation, and a square wave may favor larger magnitude frequencies. Moreover, it is currently believed that cold stimulation leads to reduced phasic firing rates and warm stimulation leads to increased phasic firing rates. In some embodiments, time-varying thermal waveforms may be selected for administration based on a region of the brain in which stimulation is desired. In some embodiments, different thermal waveforms may be used in respective ears. For example, a warm treatment waveform that oscillates between warm temperatures in one ear and a cold treatment waveform that oscillates between cold temperatures in the other ear may increase a stimulation into a particular region of the brain. However, it should be understood that any suitable combination of waveforms may be used. In some embodiments, waveforms are varied over the same or different treatment periods. For example, various thermal waveforms, including, but not limited to, those described in U.S. Provisional Patent Application Nos. 61/424,13261/498, 096, 61/424,326, 61/498,080, 61/498,911 and 61/498,943 may be used In some embodiments, two eigen functions or general shapes for time-varying thermal waveforms may be used: the square wave and the sawtooth (or triangular) wave. Both of these waveforms vary in time, which may be useful to maintain robust vestibular stimulation for time periods that may be therapeutically useful. In addition, these waveforms may employ periods of stasis or continuous variability. For example, in the case of the square wave, a specific temperature is applied to the ear canal and that stimulation may set up a heat flow pattern that may be eventually propagated over to the proximal wall of the ear canal. However, the period of stasis should not be so long that the cupula adapts to a new position, which may result in a return to the tonic firing rate, which typically occurs in about 2-3 minutes during constant temperature applications such as that delivered by traditional diagnostic caloric irrigators or other caloric devices that typically do not apply time-varying waveforms. In contrast, a sawtooth waveform constantly varies, and thus the cupula may be always out of equilibrium and the phasic firing rate may be continuously varying. However, if the change in temperature of the sawtooth waveform is too small or the rate of change is too fast for the bony structure of the ear to keep up, the variations in temperature will tend to be homogenized, and an insufficient thermal gradient may be established, for example, across the horizontal semicircular canal and other vestibular structures such as the utricle and saccule.

In some embodiments, the frequency or period of the waveform may not be constant and/or may be irregular, e.g., so as to introduce "noise" into the caloric stimulation. The variations in frequency/period of the waveform can be stochastic variations (i.e., a random variation in frequency), structured variations (such as based on a function, e.g., "1/f noise"), or monotonic variations. Although in conventional electrical neurostimulation, the frequency of the stimulation may be rapidly varied, for calorics, the thermal conduction time may limit the speed with which one can vary the frequency. Without wishing to be bound by theory, injecting low frequency noise (e.g., 2 Hz or less) may improve a therapeutic benefit. In some embodiments, the frequency/period may be changed from one session to the next. Moreover, the variations in frequency/period may be independently controlled such that different periods/frequencies may be used or varied differently in each of the patient's ears.

In some embodiments, the time-varying thermal waveforms are sufficient to induce nystagmus over periods longer than about four or five minutes or for longer than ten to fifteen minutes or more. Nystagmus may be as measured by videonystagmography and/or by electronystagmography, and may increase or decrease or even cease for brief periods over the treatment period, but may be substantially present over four or five minutes or for longer than ten to fifteen minutes or more. As noted previously, it should be understood that nystagmus may be induced by the delivery of time-varying thermal waveforms as described herein; however, vestibular stimulation may also be present in which no nystagmus is induced according to some embodiments.

Nystagmus generally refers to involuntary eye movements enabled by the vestibulo-ocular reflex (VOR) or loop. The starting point of the loop is afferents leaving the vestibular bodies, going to the vestibular nuclei in the brainstem. From the brainstem the loop continues through the cerebellum and to the motor cortex controlling eye movements as would be understood by one of skill in the art. The VOR makes possible the tracking of an object with one's eyes while the head is moving, for instance. In this case, input from the horizontal semicircular canal may be primarily responsible for such tracking to be possible. Rotating the head about the vertical axis deforms the cupula in the horizontal SCC and alters the tonic firing rate of the afferent nerves and innervating the hair cells associated with the horizontal SCC. Head rotation in one direction increases the (phasic) firing rate above the tonic rate and head rotation in the opposite direction decreases the firing rate.

Without wishing to be bound by theory, caloric vestibular stimulation may provide an artificial mechanism to activate the VOR. By tilting the head (~20 degrees above the horizontal), the horizontal SCC is placed in a vertical orientation. Creating a differential temperature across this canal may result in convection currents that act to displace the cupula. Warm caloric vestibular stimulation may lead to cupular displacement such that the phasic firing rate increases, whereas cold caloric vestibular stimulation may lead to a decrease in the firing rate. Further, warm caloric vestibular stimulation may lead to nystagmus that is manifested by a rapid movement of the eyes towards the simulated ear. Cold caloric vestibular stimulation may result in the rapid phase of nystamus away from the stimulated ear. Therefore, by noting the existence and the direction of nystagmus, it may be determined that the VOR is being activated and whether the phasic firing rate is greater than or less than the tonic firing rate. In some embodiments, the results of nystagmus may be used to select a therapeutically effective treatment waveform, including the introduction of variations, such as noise, as described herein.

The use of continuous caloric vestibular stimulation irrigation or stimulation at a constant temperature may induce nystagmus. However, after a time on the order of 2-3 minutes (e.g, Bock et al., "Vestibular adaptation to long-term stimuli," Biol. Cybernetics, vol. 33, pgs. 77-79, 1979), the cupula may adapt to its new, displaced position and the phasic firing rate typically returns to the tonic rate. Thus, nystagmus will effectively cease and the vestibular nerve afferents will no longer be stimulated.

In some embodiments of the current invention, the use of time-varying thermal waveforms enables the persistent stimulation of the vestibular nerve afferents, beyond the time period at which adaptation to a constant thermal stimulus occurs. In contrast to continuous caloric vestibular stimulation, time-varying thermal waveforms may allow for stimulation for a longer or even an indefinite period of time. However, treatments of about 10-20 minutes may be therapeutically effective.

Moreover, different waveforms may be delivered to the ears such that one waveform at least partially counteracts the nystagmus induced by the other waveform in the opposite ear. Stated otherwise, a caloric output delivered to one ear (in the absence of a caloric output being delivered to the other ear) may be configured to induce an observable degree of nystagmus of the subject. Another caloric output delivered to the other ear (in the absence of a caloric output being delivered to the first ear) may be configured to induce another observable degree of nystagmus of the subject. When the two caloric outputs are delivered simultaneously, however, a reduced degree of nystagmus occurs in relation to what would normally occur when only one or the other is delivered to a subject. That is, the degree of nystagmus that is induced that is less than the degree of nystagmus induced by either caloric input when delivered in the absence of the other. In some embodiments, the reduced degree of nystagmus comprises essentially no net horizontal nystagmus and a relatively slight vertical nystagmus.

Again without wishing to be bound by any particular theory, it is currently believed that two different waveforms may be delivered simultaneously and selected such that the induced nystagmus from either waveform is reduced or eliminated. Accordingly, the vestibular system may be stimulated while certain effects of vestibular stimulation, such as vertigo and other dizziness or nausea, may be reduced or eliminated. Nystagmus may be induced by the delivery of time-varying thermal waveforms as described herein; however, vestibular stimulation may also be present in which very little or no nystagmus is induced, such as when dual waveforms result in a nystagmus cancellation effect. In some embodiments, other effects of vestibular stimulation, such as nausea, vertigo or dizziness may be reduced or eliminated when dual waveforms are configured to result in reduced or eliminated nystagmus.

Figure 21:
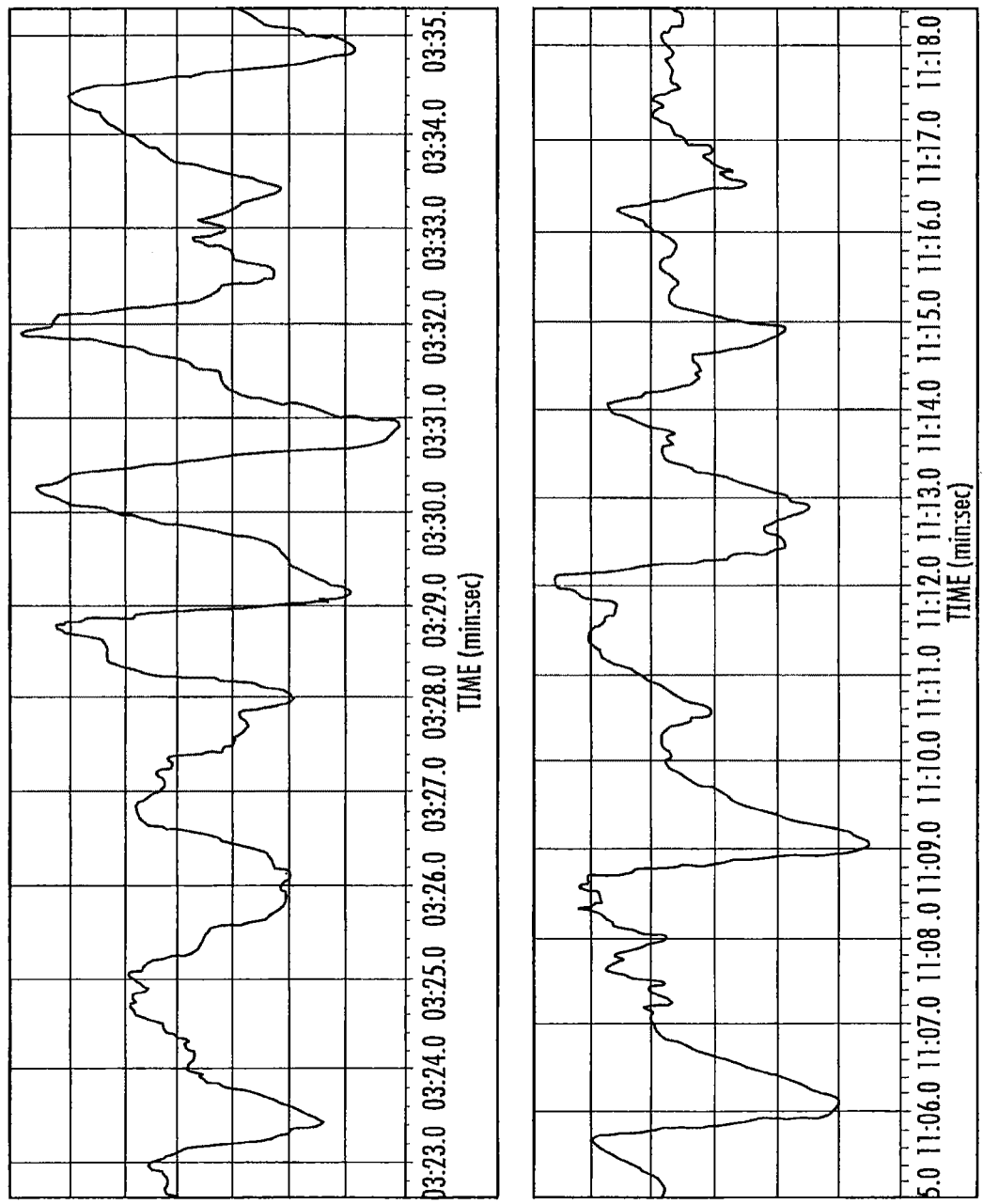
FIG. 21 is a graph of nystagmus measured by electronystagmography according to some embodiments of the present invention.

In one example, a sawtooth waveform going between temperatures of 34 to 20° C. was applied to the right ear of a subject who was reclined such that his head was ~20 degrees above the horizontal. Electronystagmography was used to measure the movement of his eyes. Segments of the time series of the nystagmus are shown in FIG. 21, demonstrating the existence of nystagmus both early in a 12 minute period and near the end of the 12 minute period. Accordingly, nystagmus may be used to confirm vestibular stimulation during a treatment period.

Although nystagmus may be used to confirm vestibular stimulation during a treatment period, it should be understood that other techniques may be used, such as medical imaging techniques. Moreover, in some embodiments, nystagmus from the stimulation of one ear canal may be nulled by stimulation using an appropriate waveform in the other ear canal; therefore, vestibular stimulation may still occur even in the absence of observed nystagmus.

Example Waveforms

Exemplary waveforms that may be delivered by the TEDs 30 of the earpieces 100A, 100B by the waveform module 220 are illustrated in FIGS. 9-15. The waveforms on the left side of FIGS. 9-15 are generally administered into the left ear, and the waveforms on the right side of FIGS. 9-15 are generally delivered into the right ear. However, it should be understood that the treatment waveforms may be delivered into either ear, e.g., so that the waveforms on the right side of FIGS. 9-15 may be administered into the right ear, and the waveforms on the left side may be administered into the left ear.

Figure 9:
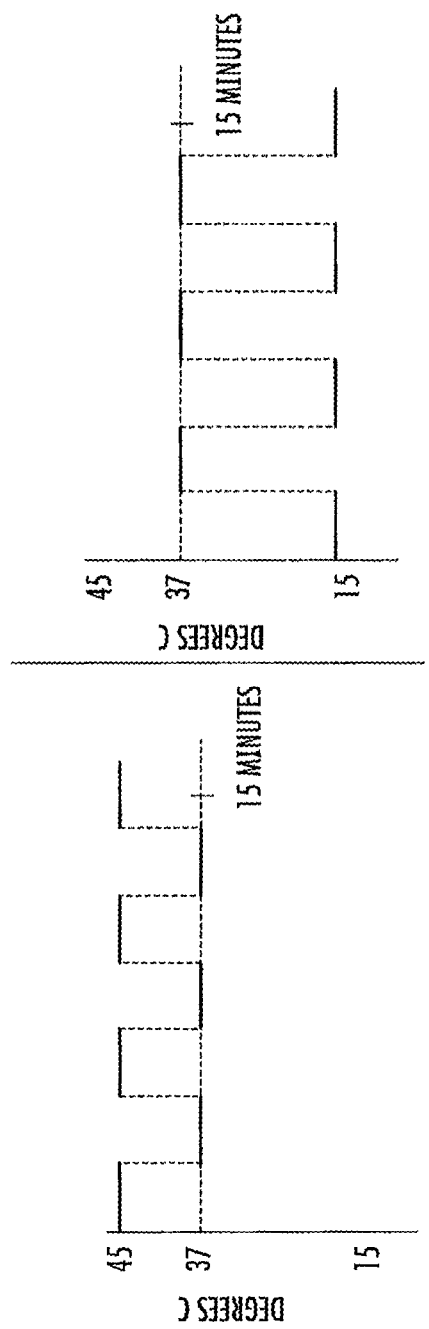
FIGS. 9-20 are exemplary treatment waveforms that may be delivered using a bilateral caloric vestibular stimulation device according to embodiments of the present invention.
Figure 10:
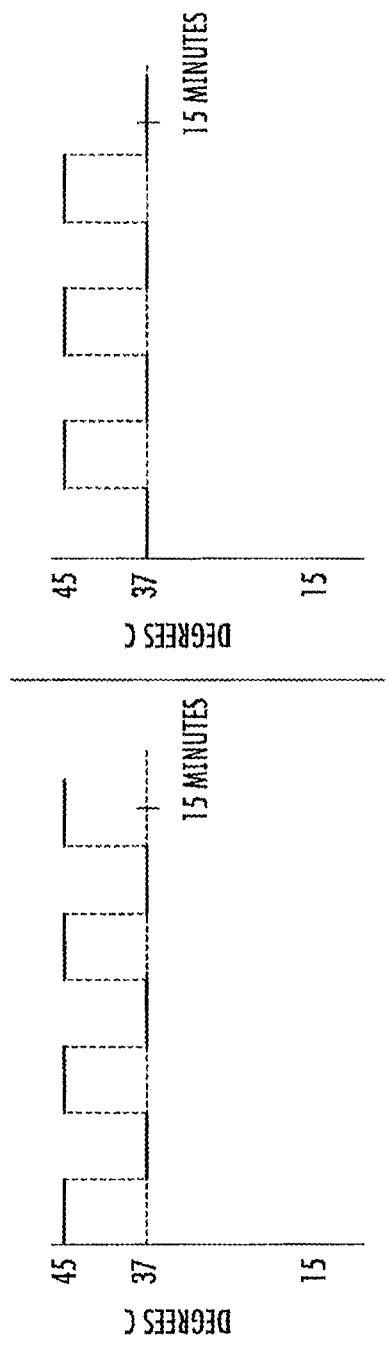
Figure 11:
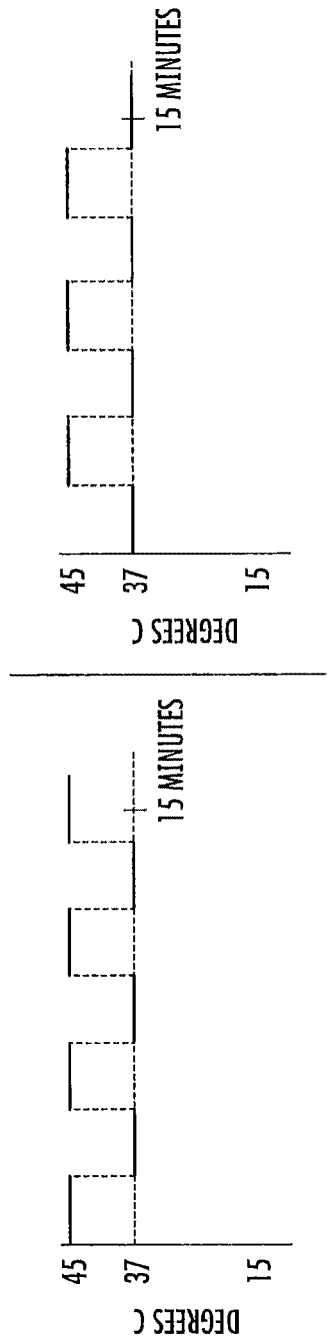
Figure 12:
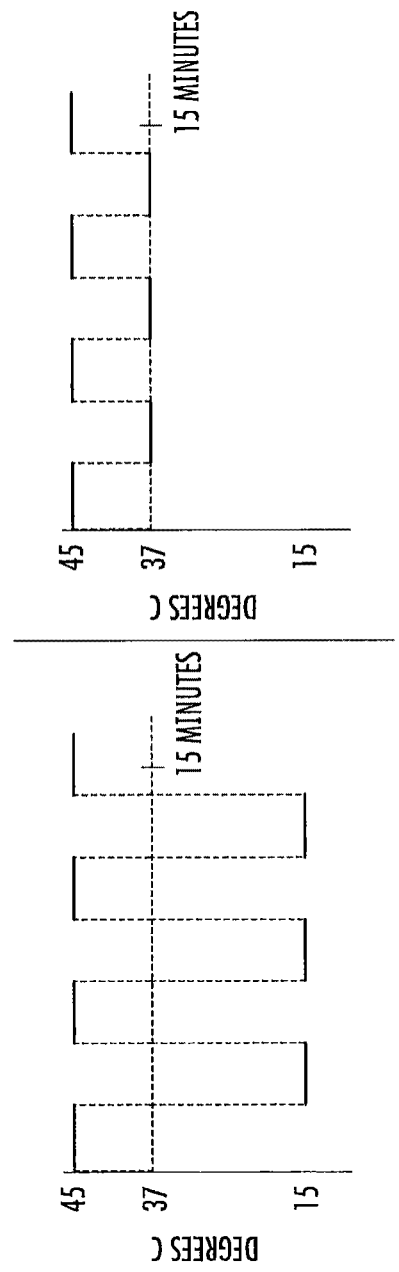
Figure 13:
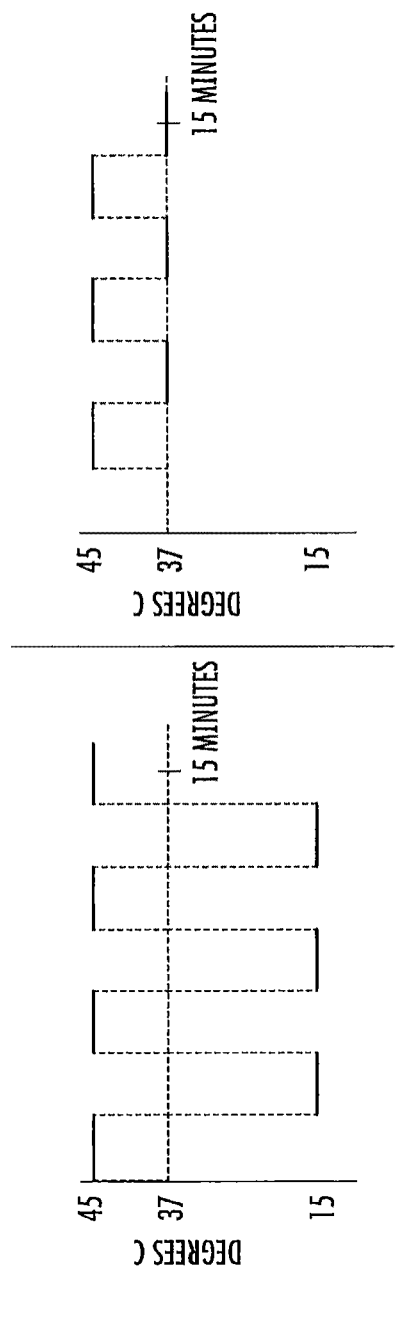
Figure 14:
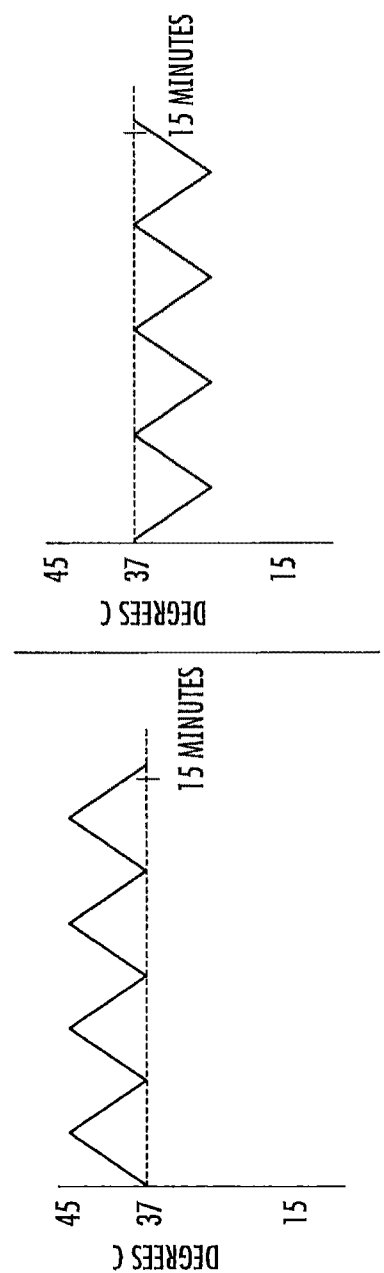
Figure 15:
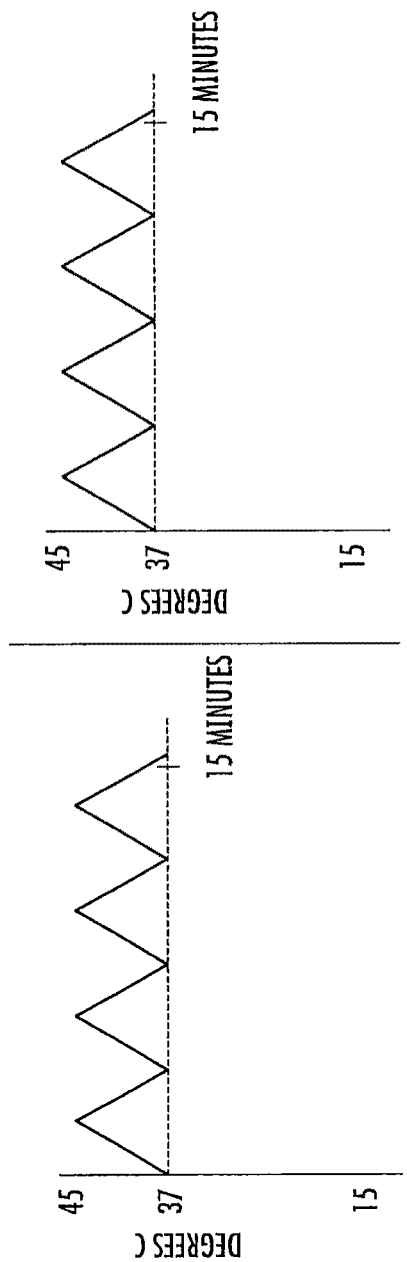
Figure 16:
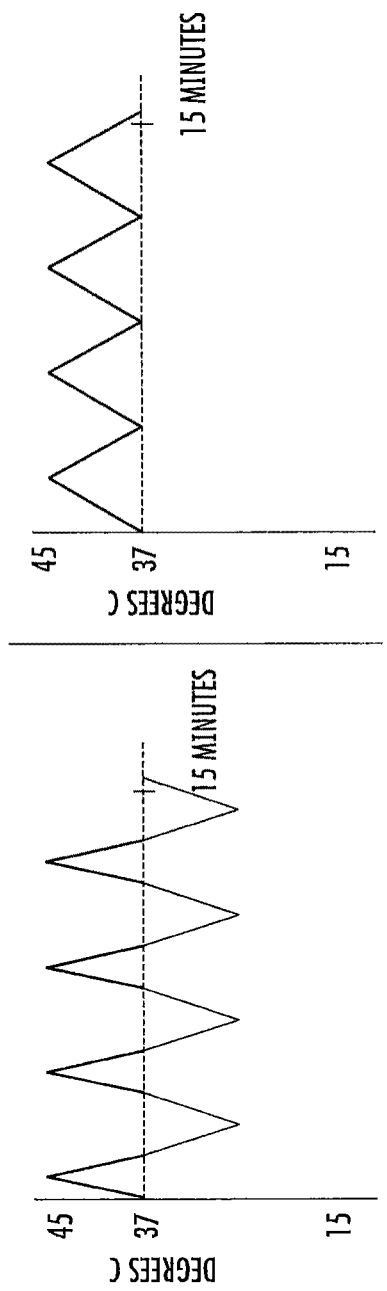

FIG. 9 illustrates in-phase square waves, with warm left ear and cold right ear stimulation, which may provide enhanced left hemispheric activation with predominantly higher and predominantly lower phasic frequencies. FIG. 10 illustrates in-phase square waves with warm left and right ear stimulation, which may lead to bi-lateral hemispheric activation with predominantly higher phasic frequencies. FIG. 11 illustrates out-of-phase square waves with warm left and right ear stimulation, which may lead to bi-lateral hemispheric activation with predominantly higher phasic frequencies, but with the maximum phasic frequency being reached at different times in the two hemispheres during a treatment session. FIG. 12 illustrates in-phase square waves in which warm and cold are administered to the left ear, and warm stimulation is provided to the right ear, which may lead to predominantly higher phasic frequencies being achieved in both hemispheres, but also with a predominantly lower phasic frequency component in the right hemisphere. FIG. 13 illustrates out-of-phase square waves with warm and cold stimulation in the left ear and warm stimulation in the right ear, which may lead to bi-lateral hemispheric activation with predominantly higher phasic frequencies being achieved in both hemispheres at different times in the treatment cycle, but also with a predominantly lower phasic frequency component in the right hemisphere that is roughly in phase with the predominantly higher phasic frequencies in the right hemisphere. FIG. 14 illustrates an in-phase sawtooth wave with warm stimulation in the left ear and cold stimulation in the right ear, which may lead to enhanced left hemispheric activation with a range of phasic frequencies being achieved both above and below and equilibrium or unstimulated rate. FIG. 15 illustrates an in-phase sawtooth wave with warm stimulation in both the left and right ear, which may lead to bilateral hemispheric activation with a range of phasic frequencies above the tonic or unstimulated rate. FIG. 16 illustrates sawtooth waves having an equal period with warm and cold stimulation in the left ear and warm stimulation in the right ear, which may lead to bilateral hemispheric activation with a range of phasic frequencies being achieved.

Figure 17:
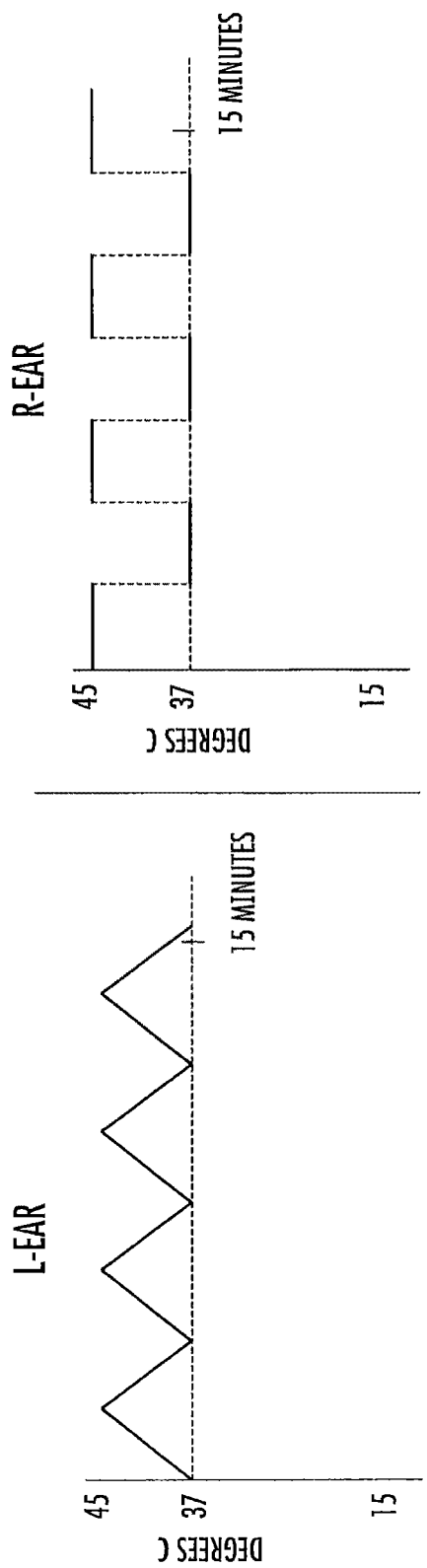

In some embodiments, different waveform shapes and/or periods may be delivered to respective ears of the patient. For example, FIG. 17 illustrates an in-phase sawtooth left ear waveform and a square wave right ear waveform that are both warm stimulations and may lead to bilateral hemispheric activation with a range of phasic frequencies being achieved above the tonic rate in the left ear and predominatntly higher phasic frequencies being achieved in the right ear. Additional configurations of other "unmatched" waveform shapes and/or periods may be used.

Figure 18:
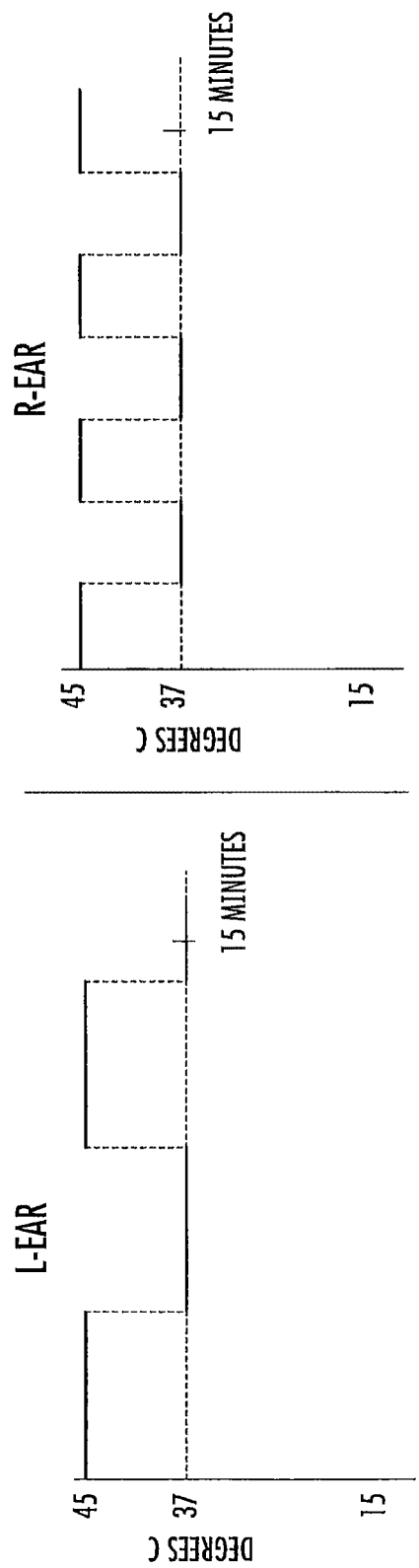
Figure 19:
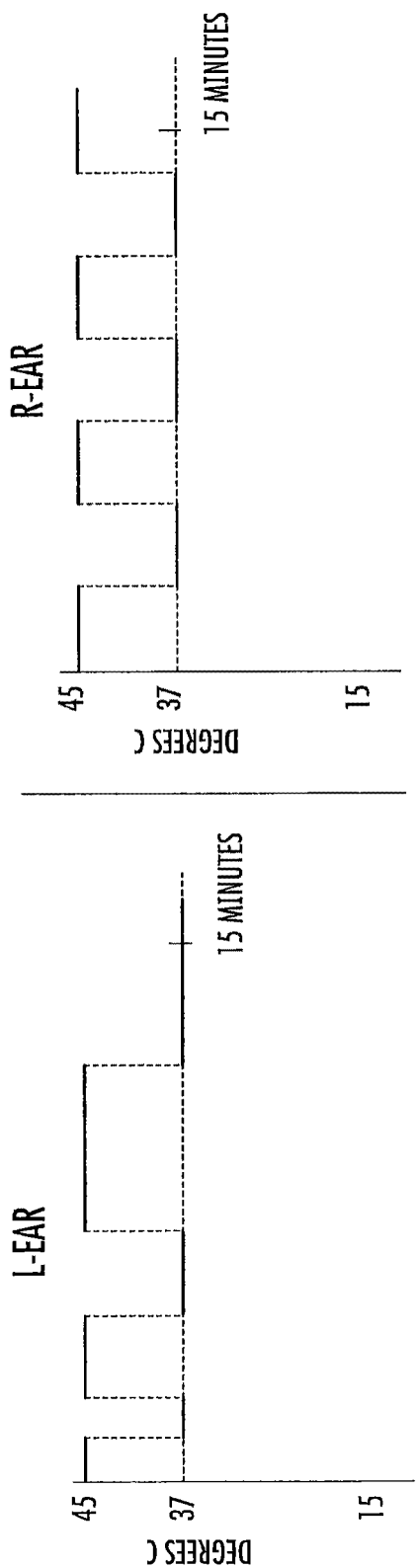
Figure 20:
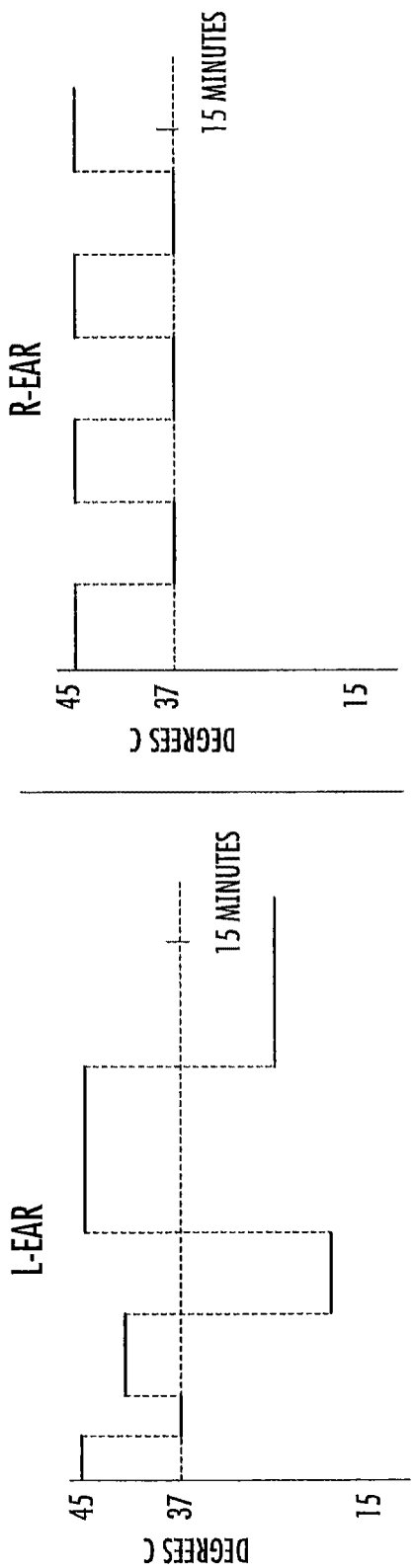

FIG. 18 illustrates square wave right and left ear warm square waves with a higher frequency square wave being administered to the right ear. This may lead to bilateral hemispheric activation with predominantly higher phasic frequencies and with the lower frequency left ear waveform resulting in a higher phasic frequency firing of the vestibular nerve than the higher frequency right ear waveform. FIG. 19 illustrates a warm left ear and warm right ear square wave with a time-varying period in the left ear. The waveforms in FIG. 19 may lead to bilateral hemispheric activation with predominantly higher phasic frequencies, but with the changing frequency of the left ear waveform leading to a variation in how long the higher phasic rate is maintained in the left ear stimulation. FIG. 20 illustrates a square waveform of both warm and cold stimulation in the left ear with a time-varying waveform period and a regular period, warm, square wave form in the right ear. The waveforms in FIG. 20 may lead to bilateral hemispheric activation with predominantly higher phasic frequencies in both hemispheres but with generally lower phasic frequencies in the right hemisphere. The temperature change in the left ear may lead to different phasic frequencies being achieved (above and below the tonic rate). The frequency variation may affect the time over which a given phasic frequency is achieved. The waveforms in FIG. 21 may lead to bilateral hemispheric activation with predominantly higher phasic frequencies in both hemispheres but with generally lower phasic frequencies in the right hemisphere. The frequency variation in the left ear may be randomly changed over time or the frequency variation may be structured, for example, increasing or decreasing over time be a given rate.

It should be understood that the treatment waveforms that may be provided are not limited to those in FIGS. 9-21. For example, the right ear stimulation and the left ear stimulation may be reversed, the shape and/or period of the waveform may be changed, and/or the warm/cold characteristics may be reversed. Without wishing to be bound by any particular theory, functional imaging studies have shown that there may be a dominant, but not complete, laterality to caloric stimulation. For example, cold caloric stimulation may have a tendency to activate contralateral brain regions and warm caloric stimulation may have a tendency to activate ipsilateral brain regions (above the vestibular nuclei in the brainstem). Marcelli et al. ("Spatio-temporal pattern of vestibular information processing after brief caloric stimulation," Eur J Radiol, vol 70, pg. 312-316, 2009) discusses that left ear, short stimulation leads to right brain activation. Accordingly, independent dual ear stimulation may allow for interesting combinations to target specific regions and hemispheres of the brain. Moreover, warm stimulation may increase the phasic firing rate of the afferents of the vestibular system and cold stimulation may decrease phasic firing.

For example, FIGS. 9-21 generally illustrate sawtooth (or triangular) wave forms and square waveforms. It should be understood that these wave forms are illustrative, and any suitable shape of waveform may be used. Both of these waveforms vary in time, which may assist in maintaining robust vestibular stimulation for times of therapeutic utility. Square and sawtooth wave forms may also embody the two primary types of variation: periods of constancy or continuous variability. In the case of the square wave, a specific temperature may be applied to the ear canal, which provides a heat flow pattern that is eventually propagated over to the proximal wall of the inner ear and thus the first of the vestibular structures of interest (the horizontal semicircular canal or "SCC"). The horizontal SCC may develop a temperature gradient across its diameter, which may drive the convective endolymph motion and distortion of the cupula. The square wave may "switch" temperatures before the cupula accommodates a terminal position and thus ceases to alter the tonic firing rate of its associated hair cells. In the interim, a pseudo-equilibrium condition may be established with heat flow. By contrast, the sawtooth waveform is generally constantly varying and thus the cupula may be in a state of being always out of equilibrium, and consequently, the phasic firing rate may be continuously varying. A potential limitation of a sawtooth waveform is that if the amplitude (or temperature delta) is too small or the rate of change is too fast for the specific heat of the bony structure of the ear, the variations in temperature may be homogenized and an insufficient thermal gradient may be established across the horizontal SCC.

Therefore, in general, the activation for a given temperature above or below body temperature is generally a lateral relationship, and a sawtooth may be useful for covering the spectrum of phasic frequencies, and the square wave may be useful for providing the larger magnitude (farther away from the tonic firing rate) frequencies. Cold temperatures (i.e., lower than body temperatures) may lead to phasic firing below the tonic rate and warm temperatures (i.e., above body temperatures) may lead to phasic firing above the tonic rate (in the horizontal SCC). Various examples are provided in FIGS. 9-21.

It may also be noted that a variety of stimulation combinations, which may be provided according to embodiments of the present invention, may address challenges that may be presented by electrical neurostimulators (including implanted electrode devices and transcranial magnetic stimulation devices). Adaptation to neurostimulation is discussed, e.g., by Krack et al., "Postoperative management of subthalamic nucleus stimulation for Parkinson's disease," Movement Disorders, vol. 17, pg. S188, 2002. For instance, for an implanted neurostimulator that is generating a specific pulse train for many hours during the day over many days, the tendency is for synaptic plasticity to accommodate this new stimulus and potentially decrease the efficacy of the therapy. Some modern neurostimulators attempt to include adaptive changes to the stimulation to account for changes in efficacy, but such systems work under a narrow range of parametric settings and the risk of side effects developing from changes in the stimulation pattern is significant. Side effects resulting from caloric stimulation according to some embodiments of the present invention may be transient and easily observed, and thus. the prescribing medical health professional can try a range of treatment paradigms to balance continued efficacy and low side effects.

In some embodiments, waveforms may be altered over time so as to reduce adaptation by the nervous system and provide continued efficacy over time.

Although various examples of waveforms are provided in FIGS. 9-21, additional waveforms may be provided by varying one or more of the following parameters:

| Parameter | Control |
| --- | --- |
| Δ temperature | Control of the TED's upper and low temperature ranges |
| Δ frequency | Software programming that allows time-varying waveforms to be created |
| Vary freq. during treatment | Software programming that allows time-varying waveforms to be created |
| Vary range of Δ temp. during treatment | Software programming that allows time-varying waveforms to be created |
| Time-varying waveform type | Software programming that allows time-varying waveforms to be created |
| Phase relationship between left and right applied waveforms | Timing relationship between the independent waveform controllers for the left and right earpieces |

-continued

| Parameter | Control |
|---|---|
| Stochastic or structured noise modulation of waveform temperature, frequency, or phase | The ability to import a designed waveform into the waveform controllers |

Again, without wishing to be bound by any particular theory, the human body is currently believed to have naturally developed systems that are not strictly periodic in terms of activation or neuronal spiking. For example, the power spectrum of EEG measurements has a slope that is close to 1/f (the inverse of the frequency). This may imply that the dynamical system underlying the EEG spectrum (the summation of all cortical neural activity) has properties like scale similarity (one part of the EEG power spectrum, when expanded, looks like the whole spectrum) and self-organized criticality, which may imply that the state of the system is in a sense poised between predictable periodic behavior and unpredictable chaos (see, e.g., Buzsaki, "Rhythms of the Brain," Oxford Press, 2006). There are also well-studied pathological conditions reflecting abnormal synchronous behavior, such as cardiac fibrillation and epileptic seizures. Neurostimultors have made use of random (stochastic) or aperiodic (structured noise, like 1/f noise) pulse sequences to evaluate enhanced efficacy. For example, instead of maintaining a 100 Hz electrical firing rate the frequency might be varied with structured or unstructured noise. Caloric vestibular stimulation may act to modify the phasic firing rate of the hair cells indirectly by, primarily, modulating the position of the cupula. Thus, to introduce noise into the phasic firing rate, a time-varying thermal waveform may be provided to move the cupula in a way such that the transduced effect is to produce the desired phasic firing frequency spectrum. As a specific example, the summation of five sine waves is considered. A sine wave may be used as a basis function from which time-varying thermal waveforms may be created. In fact, the sawtooth wave considered herein may be provided by a series of sine waves (e.g., a Fourier series). The amplitude as a function of time is:

$$A(t) = \frac{2}{\pi}\sum_{k=1}^{\infty}\frac{\sin(2\pi k f t)}{k}$$

Figure 22:
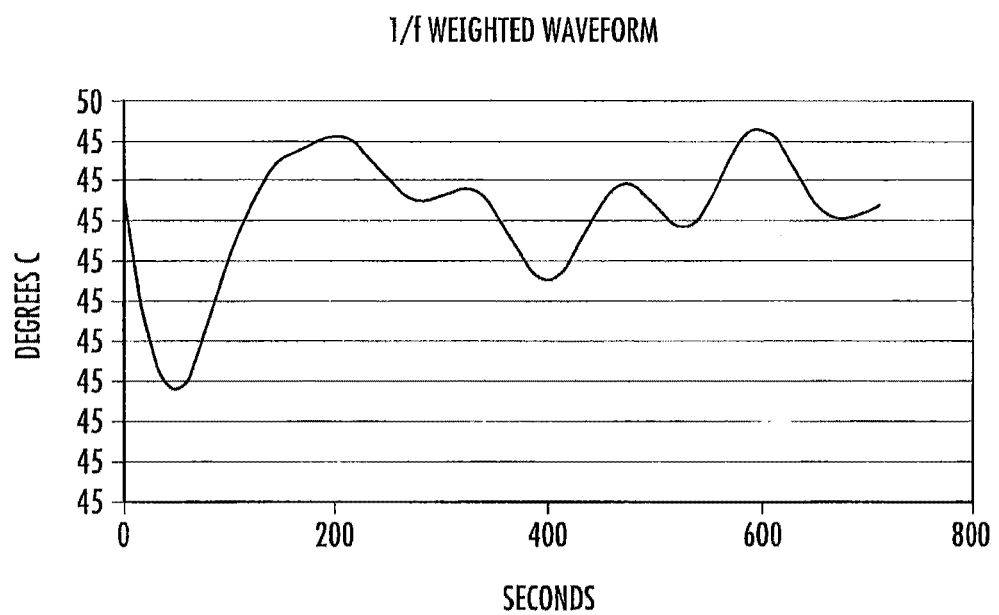
FIG. 22 is a graph of a 1/f weighted waveform over time according to some embodiments of the present invention.

Now, for the example of the summation of five sine waves, 1/f weighting is included as follows:

$A(t)=(1/f_1)*\sin(2pf_1 t)+(1/f_2)*\sin(2pf_2 t)+(1/f_3)*\sin(2pf_3 t)+(1/f_4)*\sin(2pf_4 t)+(1/f_5)*\sin(2pf_5 t)$ wherein values of $f_{1-5}$ are chosen as follows: $f_1=0.003$ Hz, $f_2=0.004$ Hz, $f_3=0.005$ Hz, $f_4=0.006$ Hz and $f_5=0.008$ Hz, and the sign and offset of the function is adjusted. This results in the temperature profile illustrated in FIG. 22.

As discussed herein, the change in phasic firing rate is currently believed to be approximately linear with the change in caloric stimulation temperature, and therefore, the phasic rate may be changed according to the spectral character of the caloric waveform. Thus, the 1/f-weighted waveform above may induce 1/f-weighting into the phasic frequency spectrum. It should be understood that additional or alternative weighting coefficients may be used to provide time-varying waveforms according to embodiments of the present invention.

It should be understood that the treatment waveforms may be used as an adjuvant treatment, alone (e.g., monotherapy) or as neoadjuvant therapy (e.g., the delivery of a treatment waveform before or after another therapy).

Example Impedance Measurements

An Agilent® LCR meter was connected to metallic parts that roughly matched the diameter and contour of the earpieces described herein. Resistance values were taken at 1 KHz, within 10 seconds of insertion, and with either firm pressure on the ear or light pressure on the ear as follows:

| Firm Pressure (kilo-ohms) | Light Pressure (kilo-ohms) |
|---|---|
| 50 | Typical: 150-200 |
| 40 | |
| 46 | |
| Typical 40-50 | |

Capacitance values were taken at 1 KHz, within 10 seconds of insertion for firm pressure on the ear or light pressure on the ear for three subjects as follows:

| Firm Pressure (pF) | Light Pressure (pF) |
|---|---|
| 3500 | 1700 |
| 3500 | 1700 |
| 3500 | |

Comparative capacitance values were measured on the pinna at ~600 pF and on the outer ear canal at ~500 pF. Therefore significantly higher values for both capacitance and resistance were measured when firm pressure was applied to the device to improve contact with the ear canal.

In addition, three different subjects were tested for both capacitance and resistance with firm pressure, which yielded values within a consistent range. The test values were C=3.5-3.9 nF and R=30-32 k-ohm for the first subject, C=3.7-4.0 nF and R=20-24 k-ohm for the second subject, and C=3.5-4.0 nF and R=35 k-ohm for the third subject.

Thus, the capacitance values seemed generally consistent when hard pressure was used. The resistance values seemed more variable, but still provided a consistent range of values with firm pressure. The values recorded when one of the ear probes was placed on the pinna or outer ear canal were significantly different from both firm pressure and light pressure reading well into the canal. Such measurements may be used, e.g., by the impedance module 222 in FIG. 8 to verify earpiece placement and thermal contact and/or to verify patient compliance with applying the treatment waveforms during operation of the earpiece in the ear canal.

Example Treatment Protocols

Embodiments according to the present invention will now be described with respect to the following non-limiting examples Example 1

Long Duration Square Wave Administration

A male subject in his forties and good health, naïve to CVS treatment, was administered cold caloric vestibular stimulation to his right ear in a square waveform pattern. The pattern was of cooling to 10 degrees Centigrade (as compared to normal body temperature of about 37 degrees Centigrade) as a "step" function or "square wave" with one symmetric square wave being delivered for a time period of 20 minutes. The subject was observed by others to be slurring his words, and was asked to remain seated for a time of two hours following the treatment session as a precaution. Otherwise, no long-term deleterious effects were observed.

Example 2

Sawtooth Wave Administration

The same subject described in EXAMPLE 1 was subsequently treated by administering cold caloric vestibular stimulation to the right ear in a sawtooth waveform pattern of cooling to 20 degrees Centigrade (as compared to normal body temperature of about 37 degrees Centigrade) in a symmetric sawtooth waveform pattern, without gaps, at a frequency of one cycle or waveform every five minutes, for a total duration of approximately 10 minutes and a delivery of a first and second waveform. Unlike the situation with the square wave pattern described in Example 1, the subject continued to perceive the temperature cycling up and down.

Example 3

Maximum Waveform Amplitude

The same subject described in Examples 1-2 was administered cold caloric vestibular stimulation to the right ear as a sawtooth cooling waveform at different amplitudes in a titration study. A maximum perceived sensation of cyclic cooling was perceived at a peak amplitude of about 17 degrees Centigrade (or cooling from normal body temperature to a temperature of about 20 degrees Centigrade). Cooling beyond this did not lead to additional gains in the sensation of cyclic cooling perceived by the subject.

Example 4

Minimum Waveform Amplitude

Modeling of the human vestibular system indicates that the cupula (the structure within the semicircular canals pushed by the movement of fluid therein and which contain hair cells that convert the mechanical distortion to electrical signals in the vestibular nerve), is stimulated by caloric vestibular stimulation at chilling temperatures of 5 or 7 degrees Centigrade below body temperature.

Example 5

Maximum Waveform Frequency

Modeling of the human vestibular system indicates that a slew rate faster than 20 degrees Centigrade per minute (which would enable one 20 degree Centigrade waveform every two minutes) is not useful because the human body cannot adapt to temperature changes at a more rapid rate. While maximum frequency is dependent in part on other factors such as waveform amplitude, a maximum frequency of about one cycle every one to two minutes is indicated.

Example 6

Minimum Waveform Frequency

Modeling of the human vestibular system indicates that a continuous, time-varying waveform is most effective in stimulating the vestibular system, as stagnation and adaptation of the cupula is thereby minimized. While minimum frequency is dependent in part on other factors such as the waveform amplitude, a minimum frequency of about one cycle every ten to twenty minutes is indicated.

Example 7

Treatment Session Duration

To permit delivery of at least a first and second waveform, a duration of at least one or two minutes is preferred. As noted above and below, results have been reported by patients with treatment durations of ten and twenty minutes. Hence, as a matter of convenience, a treatment session duration of not more than 30 or 40 minutes is preferred (though longer sessions may be desired for some conditions, such as acute care situations).

Example 8

Treatment of Migraine Headache with Sawtooth Waveforms

A female patient in her early fifties with a long standing history of migraine suffered an acute migraine episode with symptoms that consisted of a pounding headache, nausea, phonophobia, and photophobia. Right ear cold caloric vestibular stimulation was performed using the sawtooth waveform, essentially as described in Example 2 above, with a temperature maximum of 17 degrees (chilling from body temperature) for 10 minutes (for a total delivery of two cycles). At the conclusion of the treatment the patient reported that her headache and associated symptoms were no longer present. At a reassessment one day later, the patient reported that the headache had not returned.

Example 9

Treatment of Diabetes with Sawtooth Waveforms

The same subject described in examples 1-3 suddenly developed an episode of extreme urination (10 liters per day), thirst for ice water, and associated fatigue. Urinary testing suggested the onset of diabetes mellitus, for which there was strong family history.

The patient's initial weight as taken at his primary care physician indicated a recent 20 pound weight loss. The first attempt to obtain a glucose reading from the patient resulted in an out of range result (this result typically occurs with glucose levels in excess of 600 mg/dl). The patient was hospitalized and received hydration and IV insulin therapy. The patient's first glucose level after this treatment was 700 mg/dl. The glucose level were brought down to approximately 350 and treatment with an oral antihyperglycemic agent was initiated.

Follow-up care after hospital discharge with the subject's primary care physician. expanded the oral antihyperglycemic agent therapy to include both metformin and JANUVIA™ sitagliptin. In addition, a strict exercise program of 30-45 minutes 5 to 6 days per week and diet control were instituted. Daily glucose levels via finger stick were taken 2 to 3 times per day.

At this point the patient's baseline hemoglobin A1c (Hb A1c) level was 9.8%, as compared to normal levels of 5 to 6%.

The patient then began daily treatment with caloric vestibular stimulation. The treatment was carried out for a time of ten minutes, once a day for about a month, after which the treatment was continued two to three times a week for three additional months (with each treatment session being about 10 minutes in duration). The caloric vestibular stimulation was delivered to the patient's right ear, as a sawtooth cooling waveform as described in Example 2. At the conclusion of these treatments, the patient's HB A1c level was 5.3%. As a result, the patient was removed from all hypoglemic agents.

Most oral antihyperglycemic agents lower a patient's Hb A1c level by approximately 1 to 2% (see generally S. Inzucchi, Oral Antihyperglycemic Therapy for Type 2 Diabetes, *JAMA* 287, 360-372 (Jan. 16, 2002)). In contrast, this patient's initial value was 9.5, and dropped to 5.3.

Example 10

Alternate Waveform Shapes

Figure 23A:
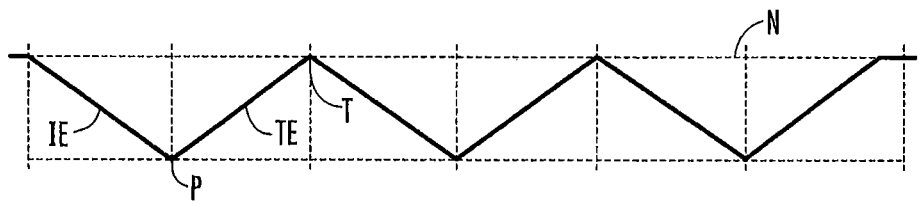
FIGS. 23A-23F are schematic diagrams of various non-limiting examples of waveform stimuli that may be used to carry out the present invention. While each line A through F illustrates several cycles of a given frequency and waveform shape, note that "waveform" herein generally refers to a single cycle of a given frequency and waveform shape.

The sawtooth waveform described in the examples above was symmetric and linear, as illustrated in FIG. 23A, where line dashed line "n" represents the subject's normal body temperature (typically about 37 degrees Centigrade). Modeling of the vestibular system indicates that waveforms of similar amplitude and frequency, but with a variation in shape, are also effective, such as the "logarithmic" or "convex" waveform of FIG. 23B, and the "exponential" or "concave" waveform of FIG. 23C. All waveforms generally include a leading edge ("le"), a trailing edge ("te"), a peak ("p") and a trough ("t").

Figure 23B:
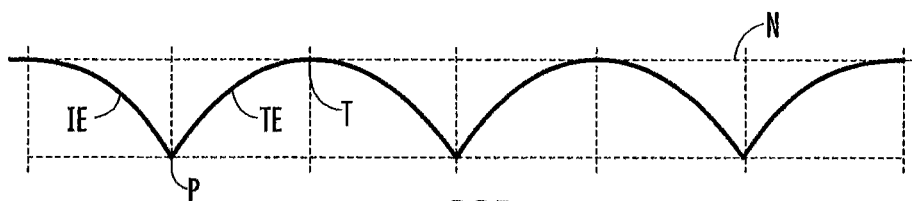
Figure 23C:
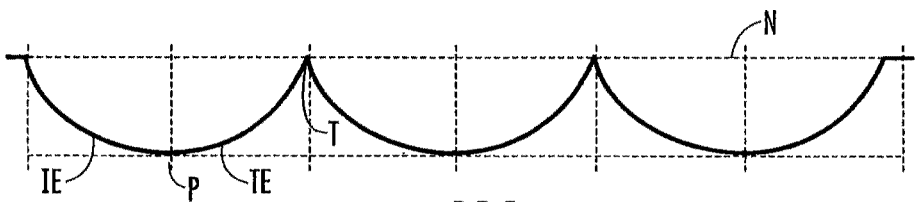
Figure 23D:
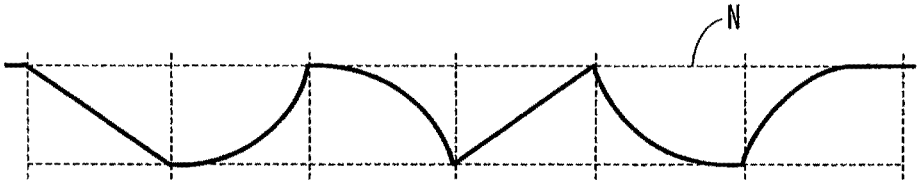

While FIGS. 23A through 23C all show three consecutive waveforms of the same shape, amplitude, and frequency, the consecutive waveforms can be varied in shape as shown in FIG. 23D, and can be varied in amplitude or duration as well (preferably each consecutive waveform within the parameters noted above), to produce still additional waveforms and sequences of waveforms which are useful in carrying out the present invention.

Figure 23E:
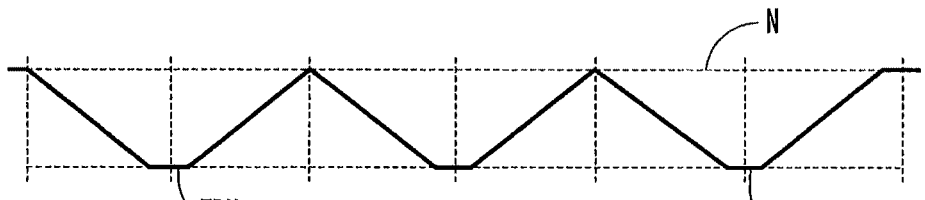
Figure 23F:
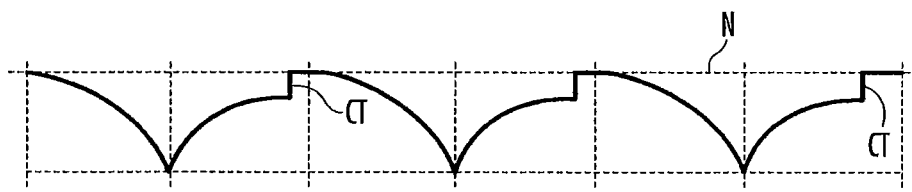

In addition, while the waveforms of FIGS. 23A through 23D are shown as continuous, minor disruptions can be included therein, such as truncations ("trn"; for example, as shown in FIG. 23E,) or vertical cuts ("ct"; for example, as shown in FIG. 23F) to produce still additional waveforms and sequences of waveforms which are useful in carrying out the present invention.

The peak for all waveforms of FIGS. 23A-23F is cooling by 17 degrees Centigrade from normal body temperature to a temperature of 20 degrees Centigrade, and the trough for all waveforms is a return to normal body temperature, giving an amplitude of 17 degrees Centigrade. The frequency for all illustrated waveforms is 1 cycle (or one complete waveform) every five minutes. While 3 cycles of the same waveform are illustrated for clarity, note that in some of the examples above only two cycles are delivered over a total treatment or session duration of ten minutes.

Example 11

Patient Orientation

It was noted that a patient who was sitting up (watching television) and receiving a cold caloric vestibular stimulation (CVS) treatment reported perceiving a different effect than perceived in prior sessions. Upon reclining to about 45 degrees, she did receive the earlier effect.

The "standard" angle of recline for diagnostic CVS is about 60 degrees (or equivalently 30 degrees above horizontal). The reason for this positioning is that the "horizontal" SCC is tilted up by about 30 degrees (higher on rostal side) (More recent x-ray measurements put the angle at closer to 20+/−7 degrees.) The intent with diagnostic CVS is to reorient the horizontal SCC so that it is substantially vertical, thus maximizing the effect of the convective flow set up by calorics.

Hence, if the subject is reclined to about 20 degrees above horizontal (and supine), then a cold stimulus leads to inhibition or a phasic rate less than the tonic rate. For a warm stimulus, this situation is reversed (phasic rate increases above tonic).

Further, cold simulation tends to activate principally the contralateral brain structures whereas hot leads to principally ipsilateral activation. For example, in V. Marcelli et al. (*Eur. J. Radiol.* 70(2): 312-6 (2009)), the authors did a left ear, cold stimulation by water irrigation and saw right-side activation in the brainstem, cerebellum, etc. The patient was presumably nearly reclined in the MRI magnet.

Empirical tests and modeling indicate that approximately 20 degrees Centigrade absolute cooling (17 degrees Centigrade below body temperature) is the lower limit beyond which the cupula is maximally deformed and therefore the phasic rate change is maximal. On the warming side, more than about 7 degrees or so above body temperature becomes uncomfortable. This level of temperature heating within the ear canal will not lead to maximal deformation of the cupula. Therefore, there is an asymmetry in terms of ability to span the full frequency spectrum of phasic firing rates. However, the increase in the phasic firing rate is not constrained in the manner of a decrease—that is, the phasic firing rate can only approach zero, relative to the tonic rate of roughly 100 Hz, whereas the phasic rate can exceed 200 Hz.

Since inverting the patient changes the sign of the inhibitory/excitatory motion of the cupula, the following can be seen: Using a cold stimulus, of 20 degrees absolute, but now orient the patient so that his head is tilted forward by from 75 to 20 degrees from the vertical position. This will invert the horizontal SCC relative to the image above and now the cold stimulus will result in an excitatory increase in the phasic firing rate. For clarity, tilting the head forward by 20 degrees makes the horizontal SCC substantially horizontal. Tilting beyond that now starts to invert it so that at 110 degrees (tilted forward), the horizontal SCC will be in a vertical orientation, but now 180 degrees flipped from what is used in conventional diagnostic caloric vestibular stimulation. So, the "general rule" for treatment of having the patient reclined by 45-90 degrees can be expanded to include "tilted forward" by 75-120 degrees.

Thus a protocol is seen where, using only cold stimulus, one can cover the entire range of phasic firing rates simply by reorienting the patient at the appropriate points during the time course of treatment.

Note that this type of inversion should also lead to an inversion in the side of the brain that is primarily activated. Specifically, if cold stimulation leads to principally contralateral activation in the "rightside up" orientation, then it should lead to principally ipsilateral activation in the "upside down" orientation.

Example 12

Thermal Modeling of Caloric Vestibular Stimulation

Equation (4) of Proctor et al. (Acta Otolaryngol 79, 425-435, 1975) can be extended for an arbitrary sequence of heating and/or cooling steps. Equation (4) is a fairly simple usage of the 1-dimensional diffusion equation. Therefore, the model is not exact. The temperature difference across the horizontal canal (i.e., the thermal driving gradient) is approximated:

$$\Delta T = \frac{A_1}{\sqrt{t}}e^{-B/t} + \frac{A_2}{\sqrt{t-t_1}}e^{-B/(t-t_1)} + \ldots + \frac{A_n}{\sqrt{t-t_n}}e^{-B/(t-t_n)} \quad (1)$$

$$A_n = \frac{-LT_n}{\sqrt{\pi a}}$$

where: and $$B = \frac{x^2}{4a}$$

L=distance across horizontal canal (mm); default=6

$T_n$=difference between applied temperature and previous temperature (° C.)

a="thermal diffusivity" of temporal bone (mm2/sec); this may vary in patients, but compact bone paths will dominate the thermal. The literature lists values from 0.14-0.25, but this is based on the onset of nystagmus as the "stimulation time." Marcelli et al. showed a much faster, actual brainstem activation time after CVS, which did not relate to the onset of nystagmus. Literature estimates for the thermal diffusivity of hard bone range from 0.45-0.55 to 1.6. A value of 0.5 is assumed here, based on x-rays of the compact, wet bone in the region of interest.

x=the effective thermal distance (mm) between external ear canal and the edge of horizontal semicircular canal; default=7.5 mm ΔT=the temperature difference across the semicircular canal (° C.); distal minus proximal temperature.

$t_n$=time at which new stimulus starts.

Default values for the constants are listed next to the definitions. CVS application times that are short compared to the response time of the patient may not be very different from a longer pulse at a lower temperature due to thermal smoothing effects. Literature reports of the maximum phasic firing rate are about 100 Hz. That is, +/−100 Hz away from the tonic firing rate, which is on the order of 100 Hz. The maximum deformation of the cupula at its center is, correspondingly, about 77 microns. Thermal gradients that imply a deformation greater than this value would tend to lead to saturation of the phasic firing rate. At the other end of the scale, the minimum detectable volume change in the SCC is on the order of 25 picoliters and this corresponds to a change in the phasic rate of roughly 0.5 Hz. This indicates a minimum temperature gradient across the SCC of ~0.02° C. The obvious requirement is that the body's homeostatic temperature regulation must ensure a constant temperature across the 6 mm wide canal to a value on that order.

Another simplification used in the model was to ignore the temperature dependence of the bulk coefficient of thermal expansion of water (with the simplifying assumption that endolymph has roughly the thermal properties of water). This assumption will lead to an apparent saturation of the phasic firing rate at higher temperature (roughly 27° C.) than will actually occur. Below body temperature, the phasic rate may not saturate until the lower 20's.

The volume of the horizontal SCC is estimated to be: 3.2E-3 cc. The change in volume due to a temperature difference ΔT is: 3.8E-4*3.2E-3*ΔT=1.22E-6 ΔT.

The volume of the "lens" of the cupula when deformed to its maximal (saturation of the phasic firing rate) extent is roughly: 4.4E-6 cc Therefore, the change in the phasic rate: Δf=27.7*ΔT in Hz.

The relationship between the applied thermal waveform and the phasic firing rate of the afferents of the vestibular branch of the 8th cranial nerve can thus be modeled for a square waveform stimulus (such as in Example 1 above), and for a time-varying, saw tooth, waveform stimulus (such as in Example 2 above).

It was noted that there is little distortion of the time-varying waveform of, as compared to the square waveform, because the body can track the more gradual temperature changes.

There is a tendency for the values to skew a small amount vertically (e.g., the temperature delta goes slightly above body temp at points). This effect appears to be non-physical and is simply a limit of the approximate model employed. The same appears true of the firing rate going positive.

The "tips" of the sawtooth waveforms appear to exceed the maximum change in phasic firing rate of 100 Hz (this is seen in the square wave as well). This may be because the coefficient of thermal expansion of the endolymph changes with temperature and was not corrected in the model above. This would result in an overestimate of the firing rate for a given temperature in the plot. Therefore, the firing rate may not, in fact, saturate (i.e., will stay below a delta of 100 HZ) at 20 C. The loss of a sense of improvement reported in Example 3 above for temperatures below about 17 to 20 degrees Centigrade may be due to the cupula of the vestibular canal "pegging" (achieving its maximal physical distortion) and the firing rate saturating.

Example 13

Treatment of Chronic Migraines and Refractory Depression

A female subject was a headache sufferer with a 10-year history of debilitating, chronic migraines, the last five being refractory. She had failed all pharmaceutical interventions. The patient underwent an occipital nerve stimulator implant for headaches, with good symptom-management for approximately one year, at which point the device was no longer effective. Co-morbid with her migraine headaches was depression, which was only partially responsive to pharmaceutical management. Subject was placed on disability from her employment.

The subject was treated using a five-day therapy paradigm consisting of daily treatments comprising a square waveform pattern of cooling to 20 degrees Centigrade, at a frequency of one cycle every ten minutes, for a total duration of ten minutes while the patient was in a reclined position of thirty degrees above horizontal. Video images of the subject were captured before, during and after each treatment session and were used to assess the effectiveness of the treatment (e.g., by assessing the patient's mood).

For all active, in-process migraine episodes, within 5-15 minutes after completion of a treatment, subject experienced pain attenuation. Chronic headache indication was alleviated on the 4th day of treatment, with concurrent progressive improvement in her mood over the course of the five days. The treatment course peaked at day 5. The subject became pain-free, with complete resolution of mood symptoms. She remained pain-free for 63 days after the therapy was completed, at which time her migraine headaches began to recur, but without return of clinical mood symptoms.

The five-day therapy paradigm was repeated. The subject responded more quickly to this second longitudinal therapy, with her chronic headaches disappearing on the 3rd day of treatment. She remained pain-free for five weeks.

Later, the patient was treated with a sawtooth waveform (lower temperature of 20° C.) employing a daily treatment duration of 10 minutes. By the end of the treatment week, the patient was pain free (using a 0-3 pain scale where 3 is severe, 2 is moderate, 1 is mild, and zero is no pain). Charted pain scores (not shown) showed improvement after treatment. All CVS treatments were to the right ear using cold stimulation. Additionally, after each treatment week, the patient stayed pain free for times varying from 2-9 weeks. The patient additionally reported feelings of high energy and resolution of co-morbid depression.

Example 14

Treatment-Associated Dizziness in Migraine Patient

The same subject described in example 8 had right ear CVS treatment using a heating, to approximately 42-43 degrees, sawtooth waveform for 10 minutes, with a contiguous repeat for an additional 10 minutes. The treatment was effective in resolving her acute migraine pain. Additionally, the treatment had a soporific effect but also caused slight dizziness. The subject did not note the feeling of dizziness in example 8 using cold stimulation.

Example 15

Treatment of Cluster Headache and Treatment-Associated Dizziness

The same subject described in example 1 underwent the same CVS treatment described in example 14. He too reported a feeling of slight dizziness that was not apparent during cold CVS stimulation.

Example 16

Vestibular Migraine Treatment in Female Patient

A female subject in her late 30's had a history of migraine with associated vertigo (vestibular migraine). The subject has a history of vestibular dysfunction and slight co-morbid depression. The subject was treated on a near daily basis, between 20-40 minutes per day, with cold stimulation (down to 20° C.) CVS before switching to warm CVS, with a maximum temperature of 48° C. All CVS treatments used a sawtooth pattern with left-ear stimulation due to more severe vestibular dysfunction in the right ear. This subject did not note dizziness as a side effect of the warm CVS treatment, suggesting that her vestibular system, due to dysfunction, is more immune to CVS (and thus she must treat more aggressively to gain benefit). A parent of the subject commented on a change in the subject's speech and "spirit" during phone conversations while using cold CVS. The switch to warm CVS resulted in additional mood and motivational elements. Colleagues commented on enhanced interpersonal interactions and an increased sense of confidence. The subject stated: "for the last couple of year I've felt as if my brain has burnt out, it feels so much better since the warm treatments."

Example 17

Vestibular Migraine Treatment in Male Patient

A male in his 40's developed sudden onset migraine with vestibular dysfunction that led to effective disability and inability to go to work. The subject was not helped by medications and sought the advice of multiple physicians at two prominent academic research hospitals. The subject was treated on a near daily basis for 10-20 minutes a day with cold CVS (down to 20° C.) CVS before switching to warm CVS, with a maximum temperature of 42° C. The subject, like the subject in example 16, did not experience dizziness with the introduction of warm CVS treatments, possibly associated with the vestibular dysfunction accompanying his migraines. CVS treatments are soporific for this patient. The subject's wife notes a pronounced change since CVS treatments were started. Whereas prior to CVS treatment the subject was loath to get out of bed, since CVS treatment the subject has returned to part-time work with his employer.

Example 18

Treatment of Diabetic Patient with Warm Sawtooth Stimulation

The same subject described in example 9 switched from cold CVS to warm CVS for the control of his type II diabetes. He treated with a sawtooth waveform that oscillated between 34 and 43° C. The average heating slew rate was typically above 40° C./min and the average cooling slew rate was typically greater than 10° C./min. Since commencing CVS therapy, the subject has stopped taking medications, which were previously necessary to maintain serum glucose near a normal range. At the time of diagnosis, the subject's A1c value was 9.8. At the time shown at the end of the chart below, that value was reduced to 5.6 (again, with no medications). A1c is viewed as a better long-term marker of diabetes control than serum glucose (it doesn't fluctuate). The normal range is about 4-6. For diabetics, the recommendation is that anything below 7 is a good target. A record of the subject's serum glucose readings (not shown) indicated possible additional improvement realized with the switch from cold to warm CVS in terms of reduced variability. The subject also had a gingival abscess during the period shown and such infections can lead to oxidative stress and impaired glucose control (see generally J. Southerland et al., Diabetes and Periodontal Infection: Making the Connection, *Clinical Diabetes* 23, 171-178 (2005)). The infection did not disrupt the subject's glucose maintenance.

Glucose readings taken at 7 AM and 10 PM; CVS treatment in evening. Treatment 1: 34 to 17 degree C. sawtooth waveform, 20 minute duration. Treatment 2: 34 to 43 degree C. sawtooth waveform, two 20 minute treatment per day. Glucose levels are more controlled with treatment 2. No other diabetes medications were in use during the testing period.

The subject reported that the warm sawtooth CVS differed slightly from the cold sawtooth CVS in that it appeared to have increased potency as noted by the feeling of increased dizziness and mild nausea, which appear consistently with each treatment. Glucose levels tend to drop 10-30 points approximately 60 minutes or more after the treatment. The subject reported that combining exercise in proximity to the TNM therapy appeared to cause a glucose decrease of 30 to 50 points.

Example 19

Treatment of PTSD Patient

A male in his mid 60's was wounded three times as a Medic in Vietnam and had a history of post-traumatic stress disorder. His manner is described as introverted and his mood depressive. After the commencement of cold CVS treatments, the subject's wife reported that he started becoming more extroverted. She reported that "she did not know who this person was speaking to her this morning"; that he was planning getting together with friends; that usually he would only do this if forced; that he expressed interest in going to Africa for a photo safari; that she started thinking "where is my husband?" After a second treatment, the subject reported continuous sleep throughout the night (usually he would usually wake up 3-4 times). He commented that "insomniacs should use this." The subject reported feeling energized. The subject was usually unable to recall dreams, but awoke with visual flashback of events in Vietnam, not unpleasant just old visual memories, and returned to sleep. The subject traditionally avoided driving but now is driving with substantially less hesitation. The subject is a serious amateur painter and both the subject and his spouse report significant positive developments in his painting style and productivity since commencement of his CVS. Upon interruption of CVS therapy, PTSD symptoms gradually returned almost to baseline one week after CVS stopped.

Example 20

Treatment of Diabetes in a PTSD Patient

The patient of example 19 has type II diabetes. After the commencement of CVS therapy he became much more responsive to oral hypoglycemics, has had to cut dose significantly (data not shown).

Example 21

Alternative Waveforms in Treatment of Diabetes and Cluster Headaches

The patient described in example 18 above was administered three different waveform CVS stimuli, as follows:

A: Cooling, by approximately 22-23 degrees, with a spike waveform for 10 minutes with a contiguous repeat for an additional 10 minutes.

B: Heating, to approximately 42-43 degrees, with a spike waveform for 10 with a contiguous repeat for an additional 10 minutes.

C: Cooling, to approximately 22-23 degrees, with a spike waveform for 10 minutes as illustrated in connection with A above, followed immediately by heating, to approximately 42-43 degrees, with a spike waveform for 10 minutes as illustrated in connection with "B" above.

The treatments seemed to have a bimodal pattern of efficacy based upon cooling or heat cycles. Both modes seem to induce a sense of motion and mild nausea associated with enhanced therapeutic efficacy for the treatment of cluster headaches and the stabilization of type II diabetes in this subject. Pattern A appeared to be the most efficacious. Increasing cycle times to thirty minutes does not appear to confer an additional benefit.

Example 22

Induction of Prolonged Nystagmus by Waveform CVS

Nystagmus is the name given to involuntary eye movements enabled by the so-called vestibulo-ocular reflex (VOR). CVS provides an artificial means to activate the VOR. By tilting the head (~20 degrees above the horizontal), the horizontal SCC is placed in a vertical orientation. Creating a differential temperature across this canal results in convection currents that act to displace the cupula. Warm CVS leads to cupular displacement such that the phasic firing rate increases whereas cold CVS leads to a decrease in the firing rate. Further, warm CVS results in nystagmus that is manifested by a rapid movement of the eyes towards the simulated ear. Cold CVS results in the rapid phase of nystamus away from the stimulated ear. Therefore, by noting the existence and the direction of nystagmus, one may determine that the VOR is being activated and whether the phasic firing rate is greater than or less than the tonic firing rate.

The use of continuous CVS irrigation or stimulation at a constant temperature will induce nystagmus, but after a time on the order of 2-3 minutes (e.g, Bock et al., *Vestibular adaptation to long-term stimuli*, Biol. Cybernetics 33, 77-79 (1979)), the cupula will adapt to its new, displaced position and the phasic firing rate will return to the tonic rate. Thus nystagmus will effectively cease and the vestibular nerve afferents will no longer be stimulated.

It is an aspect of the current invention that the use of time-varying thermal waveforms enables the persistent stimulation of the vestibular nerve afferents, beyond the time period at which adaptation to a constant thermal stimulus occurs. In this example, the present invention has been used to generate nystagmus over a 12 minute period as measured by videonystagmography and by electronystagmography. A sawtooth cooling waveform going between temperatures of 34 to 20° C. was applied to the right ear of a subject who was reclined such that his head was ~20 degrees above the horizontal. Electronystagmography was used to measure the movement of his eyes, and demonstrated the existence of nystagmus both early in a 12 minute period and near the end of the 12 minute period (data not shown).

Example 23

Effect of CVS on Regional Cerebral Blood Flow (rCBF)

The purpose of this Example is to find a robust marker of successful CVS induction of relevance to neurological treatments. The study is being performed on rats using a modified version of a dual ear CVS unit. Specifically, ear bars that are connected to TEC's are placed in the ear canals of rats that have been anesthetized. The device has dual ear stimulation capability. Methods and Results: Single ear CVS: Rat #9 received a sawtooth waveform in the right ear that oscillated between 36 and 14° C. for 60 minutes (not shown). The rat was anesthetized with isoflurane. It should be noted that anesthesia may lessen the effects of CVS to a degree. The rat was oriented horizontally, which places the horizontal semicircular canal in the vestibular bodies at a roughly 30 degree tilt upwards on the anterior side. After the end of the 60 minute right ear stimulation, the same caloric waveform was then applied to the left ear. The response of the regional cerebral blood flow was measured on the right parietal region of the skull via a laser Doppler probe affixed to the skull. Roughly 30 minutes after the start of right ear CVS, the oscillation in blood flow became pronounced. The period of the sawtooth temperature waveform is 1.9 minutes. As observed (using nearest neighbor averaging), the period of the modulation in blood flow is longer, by about 30 seconds on average (data not shown). This suggests that the driving force (the CVS) leads to modulation of the blood flow via a mechanism that stays in a non-equilibrium state. That is, the rat's response does not simply match the period of the CVS waveform and is instead adapting to it dynamically. At the end of right ear CVS, the oscillations stop. Roughly 35-40 minutes after the start of left ear CVS, clear oscillations once again appear, though diminished in amplitude relative to right ear stimulation. This is presumably due to the fact that left ear stimulation has a weaker effect on blood flow in the right portion of the brain. Serrador et al. (*BMC Neuroscience* 10, 119 (2009)) note that "connections have been found between the vestibular nuclei and the fastigial nucleus . . . followed by vasodilatory connections to the cerebral vessels."

Control Run:

The CVS device was placed on the rat, but was not activated. No oscillations in rCBF were seen (the downward drift in the flow data is due to a slight shift in the baseline of the probe).

Dual Ear, Same Waveform:

Rat #12 had CVS delivered to both right and left ears simultaneously (not shown). The waveforms were not tied in phase and tended to become out of phase during the bulk of the 60 minute treatment period. No modulations in rCBF were manifested (data not shown).

The dual ear stimulation data suggest that the application of the same waveform to both ears simultaneously acted to cancel out any net modulatory effect on rCBF. However, it is still the case that the same stimulation was given to the vestibular nuclei as when only single ear CVS was used. Nystagmus, would also not appear if the same CVS stimulation were applied to both ears since the phenomenon, mediated by the vestibulo-ocular reflex (VOR), requires a differential input to the two horizontal SCC's. Thus the absence of rCBF modulation does not mean that the fastigial nuclei (both nuclei for dual ear CVS) are not being stimulated. Rather, their combined activation yields no net effect on rCBF. Since modulation of rCBF is not a necessary aspect of CVS induced neuroprotection (it is a marker of CVS induction), CVS therapy may actually be as or more effective with dual ear stimulation.

Dual Ear, Different Waveforms:

Run 17 simultaneously applied a 34 to 44 C sawtooth waveform to the right ear (period of ~40 seconds) and a 34 to 13 C sawtooth (period ~1.7 min.) to the left ear (not shown). In this case, flow modulations were seen and they persisted well past the end of the CVS treatment period (not shown). In this case the flow effect, with different temperatures applied, not only was present but continued to oscillate after the end of the active CVS treatment.

Summary:

The vestibular systems of all mammals act in the same way. Therefore, the results of the rat study discussed above has implications for human CVS therapy as well. The conclusion from the study is that the most likely cause of the modulation seen in rCBF is that CVS does stimulate the fastigial nucleus in the cerebellum.

Example 24

EEG in Rats as a Metric of CVS Efficacy

EEG is useful in identifying cortical activation associated with CVS. Therefore, EEG is useful as a non-invasive means to titrate CVS therapy. This report summarizes EEG data acquired in a rat study.

Methods and Results:

The report on regional cerebral blood flow changes in a rat during various CVS treatments has been generated. In this summary, EEG electrodes were placed in the scalp of the rat, differential pairs being applied on either side of the midline of the skull. (data not shown).

Discussion The activity observed in the theta band was markedly different between the 3 states.

For the low flow state, activity was depressed. The high flow peaks were shifted to lower frequencies as compared to the baseline (pre-CVS). In the 0-40 Hz plot, the high and low flow peaks in the low-30 Hz range overlap whereas the baseline peak is shifted (this is likely due to a difference in somatosensory perception during CVS versus pre-CVS). The sensitivity of EEG spectra to the details of CVS delivery suggest that EEG is an effective tool for evaluating the difference between CVS waveforms and for titrating them.

Example 25

Heart Rate Variability (HRV) as a Metric of CVS Efficacy

Heart rate variability seems to be a significant marker of health and systems for measuring it non-invasively are becoming common. This report describes the use of the ithlete, a commercial HRV measurement instrument that runs as an smartphone software program, or "app."

Methods and Results:

The subject is a 40-45 year old male diagnosed with seasonal cluster headaches. The device used to measure HRV is the ithlete (HRV Fit Ltd., Hants UK)) which uses an iPhone as the recording/readout device and a chest strap with sensors that monitor heart rate. The HRV parameter is calculated via a proprietary algorithm that takes the raw heart rate data as input. Note: of course there are many devices that will measure HRV and the ithlete was chosen only as a low cost and convenient system. Proper HRV is used as a metric of proper cardiac health (good health implies adequately high HRV; e.g. Malik, "Heart rate variability: standards of measurement, physiological interpretation, and clinical use," Eur. Heart Journal, vol. 17, pg. 354, 1996). For example, Gujjar et al. have linked HRV and outcomes after acute severe stroke ("Heart rate variability and outcome in acute severe stroke," Neurocritical Care, vol. 1, pg. 347, 2004).

The CVS treatment was a 42° C. sawtooth wave applied to the left ear and a 17° C. sawtooth applied to the right ear. The treatment lasted for 10 minutes. HRV data were recorded immediately after the end of the treatment. HRV is a dimensionless measure. During the October $24^{th}$ test, average HRV dropped by 30% and on October $28^{th}$ by 27% (data not shown).

Discussion:

HRV is proposed as a marker of effective CVS induction and could thus be used as a tool for titrating CVS dosing. Pathological conditions (such as cluster headaches discussed here) can lead to elevated HRV levels. Other pathological conditions, e.g. cardiac insufficiencies, are often associated with abnormally low HRV values (for that individual).

Example 26

Treatment of Fibromyalgia

A subject (also female, age 50-55) was diagnosed with fibromyalgia 3 years ago. Multiple allopathic and homeopathic interventions provided no substantive relief. The subject has co-morbid migraine headaches.

Methods and Results:

The subject underwent CVS treatment in the right ear, with a 17 degree C. sawtooth waveform.

From September 13-19 the subject stopped CVS treatment due to significant pain and inability to function. On September 20 the subject began treatments twice per day, sometimes using a $3^{rd}$ daily treatment using the CVS parameters listed above. She realized an improvement in both migraine pain and pain from fibromyalgia. In the September 28-30 timeframe thunderstorms seemed to trigger additional migraine pain, but this abated over the following days until her pain level was barely noticeable.

The subject commented upon starting twice-a-day treatments: "I'm writing to report excellent results using 2 treatments. Last night I tried 2 consecutive treatments, and I felt great! Like I'd been to a spa and had a relaxing massage and soak in the hot tub."

The subject reported on September 26th: "This weekend I was able to work with [husband] getting 14 new bushes in the yard and picking out new paint at Lowe's to repaint the shutters on the house. I'm so very hopeful and happy. Gardening is a shared passion for us, and the first two years here, I wasn't able to even water the plants, so the ones left are real survivors! I feel like you are giving me my life back, and giving [husband] his wife back."

When the subject's spouse was asked if the CVS device was truly helpful he responded: "Nothing in the last 3 years had helped before this."

After October 6, the unit was retrieved. The subject has since returned to baseline.

Example 27

Treatment of Peripheral Neuropathy

A female subject underwent spinal surgery and sustained damage to the spinal cord. Thereafter she has had intractable peripheral neuropathy (foot pain) over a roughly 4 month period that had not responded to analgesics. The subject has obtained relief using CVS, with the extent and duration of relief depending on the device used and the waveform details. Methods and results: The subject underwent CVS treatment with the following chronology:

1. Dual ear CVS unit: L-ear, sawtooth, 34 to 20° C.; R-ear, sawtooth, 34 to 42° C., 10 min. therapy. The treatment made her very sleepy (deep sleep for 20 min). Within 30 minutes, she was pain free and stayed so for 3 days, which was extraordinary for her.

2. Single (right) ear CVS unit, sawtooth, 34 to 17° C., 10 min therapy. She realized about a 50% reduction in pain level that lasted around 2 hours.

3. Single (right) ear CVS unit, long (single rise) square wave, 34 to 48° C., 10 min. She finds that the single ear, warm treatment is better than single ear, cold treatment. She must use the device several times a day to achieve pain relief.

4. Dual ear CVS unit, L-ear 17° C. square wave, R-ear 44° C. sawtooth, 10 min. Deep sleep for 45 min (at 5 PM). Foot pain ceased.

Discussion:

The subject received extended (multiple day) pain relief from one 10 min session using dual ear CVS. Single ear CVS, using a sawtooth waveform (slower slew rate) and an early device (basically a single cold/warm square wave), led to partial pain reduction for a time limited to hours. Therefore, the dual ear CVS treatment was superior to single ear for pain reduction. This subject and another have stated that the mixed waveform, dual ear (e.g., example 4) results in more significant subjective sensations (deep relaxation/sleep for this subject, increased nausea for the other). It is unclear with this single case if the mixed waveform treatment leads to increased pain reduction efficacy (both dual ear treatments were significant).

Example 28

Single Ear Treatment of Episodic Migraine

This Example evaluates the feasibility of using a portable CVS unit in a home setting over a month or more. The hypothesis was that daily CVS treatment would reduce the overall pain level and frequency of headaches.

Methods and Results:

The subject is a 50-55 year old female with a history of 6-8 migraine headache days per month (a month is taken as 28 days when reporting on migraine frequency). The subject used a right-ear CVS device and a sawtooth waveform that went from 34° C. to 17° C. with a period of roughly 1.7 minutes. The duration of the treatment was 10 minutes per session (daily sessions, moving to every other day after about 2 weeks of treatment). The average slew rate for heating was 40° C./minute and the average slew rate for cooling was 14° C./minute.

The subject experienced a decrease in pain over the first week of therapy. (pain score data not shown). In the 40 days past the one week transitionary period, the subject had only one migraine headache (again, to qualify as a migraine it must be at a pain level of 6 or more on a scale of zero to ten and last for 4 hours or more). The one headache occurred during unusual stress associated with a transatlantic trip and disruption of work schedule upon her return. The subject also noted a subjective improvement in co-morbid depression over the treatment period.

Example 29

Titration of CVS Therapy for Type II Diabetes

The intent of this report is to show experimental evidence of the control of glucose levels by adjusting the frequency with which CVS is used in a subject with type II diabetes.

Methods and Results:

The subject is a 40-45 year old male diagnosed with type II diabetes within the last two years. As reported earlier, the subject has been able to forego the use of medications to control serum glucose levels, using CVS therapy instead. Recently, the subject has started using dual ear CVS, with a warm time-varying waveform applied to one ear and a cold time-varying waveform applied to the other. The dual ear therapy reduced the frequency with which the subject needed to use CVS in order to control serum glucose levels (data not shown). Dual ear CVS was used with a 17° C. square wave for the right ear and a 42° C. sawtooth on the left ear. Each point in the graph represents a daily measurement (consistent time during each day). The red lines show when CVS was used. As the glucose levels were tracked, they would tend to move up in between CVS treatments, thus signaling when another treatment should be applied. This feedback method should be able to be extended to other patients, using their specific glucose levels to titrate frequency and intensity of CVS treatments. This subject remains off any other medications to control glucose levels.

Discussion:

This is an update report to supplement accounts from this subject already included in the Examples above, and further shows that serum glucose is a useful metric for CVS titration.

Example 30

CVS Intensity for Different Waveforms

As the CVS treatment device has evolved, we have moved from single to dual ear stimulation and have increased the slew rate to allow waveforms to be played out at a higher frequency. This report lists subjective metrics that can be used to assess the strength of CVS stimulation for a given subject.

Methods and Results:

The subject is a 40-45 year old male using CVS therapy chronically for type II diabetes and seasonal cluster headaches. He ranks the level of intensity of the CVS experience as follows:

single ear:
  daily treatments were required to control cluster headaches and serum glucose levels
  typical treatment is a cold sawtooth wave going between 34 and 17° C.
dual ear, same waveform shape, warm and cold:
  only 1-3 treatments per week are needed to control cluster headaches and serum glucose
  typical waveform is a sawtooth going from 34 to 42-44° C. in one ear and 34 to 17° C. in the other ear.
  Not much subjective difference compared with single ear during treatment
  More pronounced dizziness upon standing
  Nausea more persistent
  Faster, more complete responses for increased pain level
  Blurred vision for 3-5 minutes (possibly nystagmus)
dual ear, different waveform shape, warm and cold:
  only 1-3 treatments per week are needed to control cluster headaches and serum glucose
  typical waveform is a sawtooth going from 34 to 42-44° C. in one ear and a square wave in the other ear going from 34 to 17-20° C.
  most potent of all types tried in terms of pain mitigation and positive mood effects (side effects do not outweigh additional benefits)
  sleep inducing
  nausea while in horizontal position
  significant nausea and brief period of poor postural control upon standing
  persistent feeling of head fullness Discussion:

The most significant metrics for CVS therapy for pain patients is its effects on pain level and relative side effects. This report recounts observations by one subject that can serve as a paradigm for how other patients can be assessed in the clinic. The right titration will involve an on-going assessment of effects on symptoms (e.g., pain) and minimization of unwanted, lasting side effects (for clarity, the side effects reported above are transient). There are tradeoffs that patients can make between efficacy with more intense side effects balanced against less frequent need to treat.

The following parameters can be varied in a dual ear system:

1. temperature (magnitude and sign with respect to body temperature)
2. waveform shape
3. frequency of waveform(s); if they are different frequencies, they could be commensurate and beat frequencies could be established.
4. relative phase of waveforms (e.g., in phase or some degree of being out of phase if they have the same frequency)
5. variable frequency during the course of a treatment (each side)

The CVS device can be programmed, in principal, to play out a different combination every day, thus frustrating any tendency of the VS of the patient to adapt to a given therapeutic waveform. This is a principal advantage of dual ear over single ear CVS.

Example 31

Treatment of Sleep Disorders/Insomnia with CVS

A common report from users of the CVS device is that they have beneficial effects in terms of sleeping soundly. It is known (e.g., Horii et al., *J. Neurophysiol,* 70, 1822, (1993)) that CVS does activate the hypothalamus. The hypothalamus in turn controls the sleep/wake cycle in mammals.

Methods and Results:

The reports of the soporific effects of CVS with subjects is variable and subjective. Listing the claims by subjects in order of frequency:

1. a relaxed feeling right after the completion of a CVS treatment
2. report of having an exceptionally complete sleep cycle on the night following a CVS treatment
3. A very powerful soporific effect that resulted in the subject falling asleep during a 10-20 minute CVS treatment and staying asleep for up to several hours.

Examples of Each of the Observations Listed Above:

1. A small pilot clinical trial was performed at a private headache clinic on patients who were being treated for migraine headache. The CVS waveform used was a sawtooth, right ear only, with the temperature oscillating between 34 and 17° C. None of the subjects fell asleep during the 10 minute CVS treatment, but commonly reported being relaxed in a way that was greater than what they would feel when lying down, in a similar position, for the same amount of time.

2. A male, age 50-55 acting as a normal test subject used single ear (right) CVS, sawtooth waveform oscillating between 34 and 17° C. He reported pleasant drowsiness after the 10 minute therapy session and then reported that he'd slept exceptionally soundly that night.

3. A subject using CVS for foot pain (see previous Example on this subject) used a dual ear CVS device: L-ear, sawtooth, 34 to 20° C.; R-ear, sawtooth, 34 to 42° C., 10 min. therapy. The treatment made her very sleepy (deep sleep for 20 min). Then again: dual ear, L-ear 17° C. square wave, R-ear 44° C. sawtooth, 10 min. Deep sleep for 45 min (at 5 PM) and had to be awakened.

In all cases, subjects reported restful sleep versus "forced" sleep and they reported no ill side effects.

Example 32

Single Ear CVS Treatment of Pediatric Epilepsy

The intent with this study was to evaluate using the Gen 2.0 CVS unit (left ear only, same earpiece but different (less powerful) TEC (thermoelectric cooler or Peltier cooler) than will be used in Gen 3 device) in a single session to observe any effects on spike activity in epileptic patients as monitored by EEG.

Methods and Results:

The subjects were treated with a sawtooth waveform that went from 34° C. to 17° C. (left ear only). Note that the actual temperature profile was not the same for all patients. For patient 3, the average slew rate on heating was around 14-15° C./min and the cooling rate dropped from about 5.8° C./min to 4.5° C./min (not shown). It can be seen that more time was required to in the second "dip" to get to 17° C. This is due to insufficient power in the Gen 2.0 CVS device.

For patient 4, the inadequate power of the unit is even more apparent. The average heating slew rate was about the same as with patient 3, but the cooling rate started at 4.2°

C./min and dropped to 3.6/min (not shown). The device failed to reach the 17° C. target temperature.

The spike rate was measured by continuous EEG before CVS treatment and after CVS treatment (data not shown). The decrease in spike rate lasted from 1-2 hours for each of the four patients. The reduction in spiking ranges from 21-32%.

Discussion: despite the underperformance of the Gen 2.0 model, primarily caused by an older, less powerful TEC and the lack of a cooling fan on the heat sink, demonstrable effects were seen in all 4 patients in terms of a reduction in spike activity that persisted past the end of the CVS treatment session. At this time, we don't have the ability to try a more advanced device (e.g., Gen 2.5) with these patients. A logical course would be to treat the patients longitudinally to see if the effects of CVS could be made more lasting. Despite the challenge of performing CVS on this population (age range from 6-10 years old), it was accomplished and there were no side effects of the treatment.

Example 33

Counter Balancing Dual Waveforms that Reduce Nystagmus.

A male subject, age 50-55, was treated with a bilateral caloric vestibular stimulation using synchronous square wave thermal waveforms for a total of 16 minutes. The temperature ramped between 42° C. and 15° C. with a slew rate of about 17° C./min during heating and cooling. The cold portion lasted roughly 3 minutes and the warm portion 2 minutes. This pattern was then repeated. The subject experienced generally no net horizontal nystagmus. The subject experienced a slight vertical or slanted nystagmus of irregular character. The same subject experienced normal horizontal nystagmus patterns during unilateral CVS with the same waveforms delivered one at a time.

Additionally, the subject experienced excessive salivation during bilateral CVS, predominantly during the periods when the slew rate was high. The subject did not experience any nausea, vertigo or dizziness during synchronous bilateral CVS. However, he did have slight feelings of nausea and dizziness for brief periods following unilateral CVS.

Example 34

Prevention of Adaptation

Figure 24A:
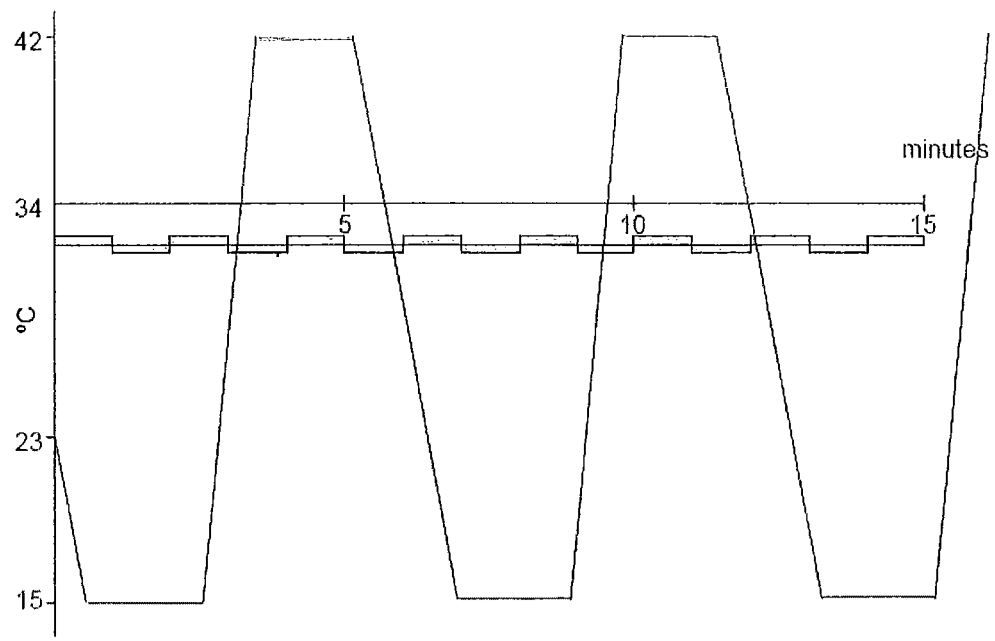
FIGS. 24A-B are schematic diagrams of a non-limiting example of a waveform stimuli for a treatment protocol that may be used according to some embodiments.
Figure 24B:
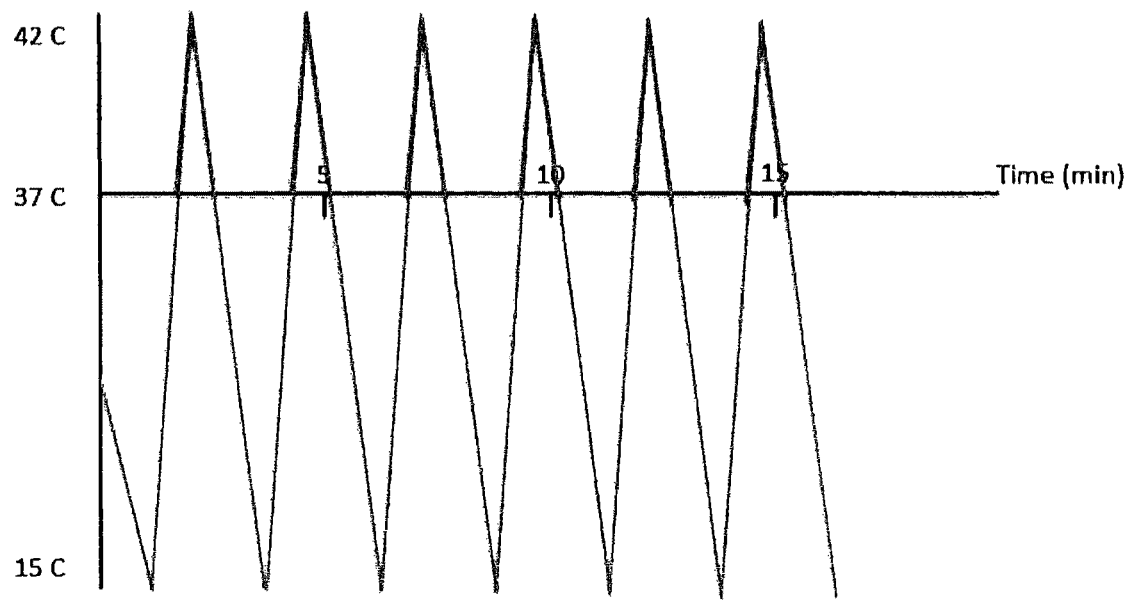

In some embodiments, various treatment protocols may be used to reduce or prevent a biological adaptation to one stimulus, which may become less efficacious if given repeatedly without treatment modification. For example, one treatment waveform may be used for number of days, such as two days, twice a day. Next, another waveform may be administered for a number of days, such as two days, twice a day. An example of the first treatment waveform is shown in FIG. 24A, and an example of the second treatment waveform is shown in FIG. 24B. This protocol may be repeated as needed to reduce or prevent adaptation to a given stimulus pattern. The total time of treatment may be about 15-20 minutes, and may be effective, e.g., for pain.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. An in-ear stimulation device for administering caloric stimulation to the ear canal of a subject, comprising:
    (a) first and second earpieces configured to be insertable into the ear canals of the subject;
    (b) at least first and second thermoelectric devices thermally coupled to respective ones of the first and second earpieces;
    (c) a first heat sink thermally coupled to the first thermoelectric device opposite the first earpiece and a second heat sink thermally coupled to the second thermoelectric device opposite the second earpiece;
    (d) an electrical connection that electrically connects the first and second earpieces, and
    (e) a controller comprising an impedance monitor configured to measure an impedance value between the first and second earpieces and to determine whether the first and second earpieces are inserted into the ear canals of the subject responsive to the impedance value.

* * * * *